US010948747B2

(12) United States Patent
Groenewege et al.

(10) Patent No.: US 10,948,747 B2
(45) Date of Patent: Mar. 16, 2021

(54) EYEWEAR AND FLEXIBLE ELEMENTS

(71) Applicant: MATERIALISE N.V., Leuven (BE)

(72) Inventors: Paulus Ludovicus Maria Groenewege, Lobith (NL); Roman Plaghki, Leuven (BE); Philippe Schiettecatte, Leuven (BE)

(73) Assignee: Materialise N.V., Leuven (BE)

( * ) Notice: Subject to any disclaimer, the term of this patent is extended or adjusted under 35 U.S.C. 154(b) by 503 days.

(21) Appl. No.: 15/738,526

(22) PCT Filed: Jul. 1, 2016

(86) PCT No.: PCT/US2016/040872
§ 371 (c)(1),
(2) Date: Jun. 26, 2018

(87) PCT Pub. No.: WO2017/004600
PCT Pub. Date: Jan. 5, 2017

(65) Prior Publication Data
US 2019/0076614 A1 Mar. 14, 2019

Related U.S. Application Data

(60) Provisional application No. 62/332,332, filed on May 5, 2016.

(30) Foreign Application Priority Data

Jul. 2, 2015 (NL) ...................................... 1041388

(51) Int. Cl.
*G02C 11/00* (2006.01)
*G02C 5/22* (2006.01)
(Continued)

(52) U.S. Cl.
CPC ......... *G02C 11/00* (2013.01); *A61M 16/0666* (2013.01); *A61M 16/0672* (2014.02);
(Continued)

(58) Field of Classification Search
CPC .......... A61M 16/0683; A61M 16/0672; A61M 16/0666; A61M 2209/08;
(Continued)

(56) References Cited

U.S. PATENT DOCUMENTS 4,465,067 A * 8/1984 Koch ................ A61M 16/0666
128/207.18
4,559,941 A 12/1985 Timmons et al.
(Continued)

FOREIGN PATENT DOCUMENTS

CA 2125790 C 9/1999
CN 103812876 A 5/2014
(Continued)

OTHER PUBLICATIONS

International Search Report and Written Opinion dated Oct. 20, 2016, in International Application No. PCT/US2016/040872.

*Primary Examiner* — George G King
(74) *Attorney, Agent, or Firm* — Patterson + Sheridan, LLP

(57) ABSTRACT

The present disclosure relates to eyewear, such as eyeglasses, configured for receiving a hose, such as a medical gas therapy hose. The eyewear comprises flexible elements and a groove defined in and extending through the flexible elements and other parts of the eyewear. The present disclosure further relates to a flexible element, such as a hinge, which may be used in eyewear to enable bending of parts of the eyewear. An exemplary embodiment of the flexible element is a hinge having a plurality of repeating units.

16 Claims, 28 Drawing Sheets

(51) Int. Cl.
*A61M 16/06* (2006.01)
*G02C 5/14* (2006.01)

(52) U.S. Cl.
CPC ....... *A61M 16/0683* (2013.01); *G02C 5/2254* (2013.01); *G02C 5/2272* (2013.01); *A61M 2209/08* (2013.01); *A61M 2209/088* (2013.01); *G02C 5/143* (2013.01); *G02C 2200/02* (2013.01)

(58) Field of Classification Search
CPC ........... A61M 2209/088; G02C 5/2254; G02C 5/2272; G02C 11/00; G02C 5/143; G02C 2200/02
USPC .................................................. 351/158, 153
See application file for complete search history.

(56) References Cited

U.S. PATENT DOCUMENTS

| | | | | |
|---|---|---|---|---|
| 5,059,017 A | * | 10/1991 | Bennato | G02C 5/008 16/228 |
| 5,193,534 A | | 3/1993 | Peppler | |
| 5,583,588 A | | 12/1996 | Chao | |
| 2008/0257343 A1 | * | 10/2008 | Peterson | G02C 11/00 128/202.13 |

FOREIGN PATENT DOCUMENTS

| | | |
|---|---|---|
| DE | 202014006155 U1 | 8/2014 |
| FR | 2700397 A1 | 7/1994 |

* cited by examiner

EYEWEAR AND FLEXIBLE ELEMENTS

CROSS-REFERENCE TO RELATED APPLICATIONS

The present application is a 371 filing of PCT/US2016/040872, filed on Jul. 1, 2016, which in turn claims benefit of U.S. Provisional Application No. 62/332,332, filed on May 5, 2016, all of which are assigned to the assignee of the present application and hereby expressly incorporated by reference herein in their entireties.

FIELD OF INVENTION

The field of the invention is eyewear comprising an eyewear hinge and/or an eyewear temple, which may be configured to receive a hose for medical gas administration, such as oxygen therapy. The eyewear may comprise a flexible element and/or a temple that enable folding of the eyewear, secure placement of the hose, and provide maximal comfort to the wearer of the eyewear. The hose is integrated into the eyewear in a manner that optimizes comfort and discretion. The present invention relates to a pair of eyeglasses, comprising a structure suitable for holding lenses, and temples. The invention further relates to assembly of such a pair of eyeglasses and oxygen administration means, the oxygen administration means comprising a tube. The invention further relates to a method for building such an assembly. The invention further relates to a tool for use in such a method. It is particular to oxygen therapy such as administered to people who suffer from COPD.

BACKGROUND

For many conditions and disorders, particularly those which affect the lungs, immediate relief of a patient's symptoms is a priority. Medical gas offers a quick and efficient way to supply therapies or medicaments to patients in need. Medical gas can be administered through face masks, nasal prongs or nasal cannula, breathing tubes, laryngeal mask airway tubes, tracheal tubes, ventilators, and more. Examples of medical gas therapy include controlled oxygen therapy, helium therapy, carbon dioxide therapy, nitrogen therapy, and hyperbaric oxygenation. Similarly, inhalational anesthetics are another example of medical gas administration.

For chronic conditions, medical gas therapy may be administered continuously. Patients suffering from chronic pulmonary obstructive disorder (COPD), bronchitis, emphysema, lung cancer, pulmonary fibrosis, pneumonia, asthma, heart failure, cystic fibrosis, sleep apnea, cluster headaches, and other lung disorders may be unable to get adequate oxygen from the air. These patients require supplemental oxygen, sometimes for as many hours as possible, typically administered through a system of hoses and nasal cannula. In this system, oxygen is delivered from oxygen sources (such as devices like gas tanks, liquid oxygen tanks which are either reservoirs or portable canisters, oxygen concentrators that are either stationary or portable, or home fill systems) equipped with long hoses and nasal prongs. A commonly-used system features nasal cannula which are connected to the oxygen source via two hoses which run along the patient's face, behind patient's ears, and under the patient's chin where the two hoses are joined into a thicker hose leading to the oxygen source. Unfortunately, this system can be uncomfortable, as the hoses can press against the patient's cheeks and cause irritation or apply pressure behind the ears of the patient and even cut into the skin behind the ears. In addition, the system is impractical for eyeglasses wearers, as there is little space behind the patient's ears to accommodate both eyeglasses and tubing. Finally, the configuration of hoses is visible on the patient's face, which can cause awkwardness in social situations. Many patients are reluctant to interact with others or to spend time in public when they are wearing the oxygen hoses. This reluctance can have consequences for their health, as some patients will forgo therapy for limited periods of time and risk oxygen deprivation, while others will avoid social situations and risk isolation, or be unable to realize benefits of light exercise and activity outside of the home.

There have been attempts in the past decades to make oxygen therapy systems more comfortable and discreet. In one approach, eyeglasses are modified with hollow channels which replace the oxygen hoses on the patient's face. However, these eyeglasses frames have several disadvantages. First, the eyeglasses frames are prone to leakage through hinges, joints, or openings in the hollow channel. Although rubber gaskets or seals can be used to minimize leakage, these rubber seals are expensive and wear out quickly. Second, some eyeglasses make use of hollow nose pieces having fixed diameters, which extend from the hollow channel in the frames and channel oxygen to the patient's nostrils. Unfortunately, as the nose pieces are often designed to be discreet, the diameter of the nose pieces may be very small and the oxygen flow is restricted. As a consequence, the air flow from the oxygen source may have to be set at a higher intensity, which can quickly drain the oxygen source and/or batteries powering the device. Third, the hollow channels are difficult or inconvenient to clean. And finally, the hollow channels cannot be readily exchanged for different sized channels without replacing the whole eyeglasses frame.

In an alternative approach, eyeglasses are modified with grooves or clips to affix oxygen hoses to the inner surface of the eyeglasses frame. While this approach offers more flexibility, none of these existing eyeglasses frames have been designed to accommodate the natural movement and bending of the oxygen hose. Thus, there remains a need in the art for an eyeglasses frame that bends in a flexible but controlled manner, and which may be configured to accommodate a standard hose for gas therapy. The eyeglasses frame may be part of a medical gas system that is comfortable, discreet, and convenient for the patient.

SUMMARY

It is known to administer oxygen therapy to people who are suffering from COPD (Chronic Obstructive Pulmonary Disease) such as chronic bronchitis, pulmonary emphysema, lung cancer, and cystic fibrosis, or for example heart failure or cluster headache. For this, so-called nasal cannula or oxygen eyeglasses can be used. A nasal cannula typically comprises two hoses, and a nose piece that is provided with two short tubular pieces which, during use, each extend about one centimeter into a nostril of the user. Each hose is connected at a first end to a source of oxygen, usually an oxygen cylinder or a so-called oxygen concentrator, and at a second end to the nose piece. During use, each of the hoses run over and behind an ear of the user.

Wearing a nasal cannula creates unwanted attention from other people. Moreover, a nasal cannula interferes with wearing (optical) eyeglasses. Also, the parts of the hose extending along the face can slide or leave marks on the face. As a solution, it has been proposed to provide the frame of (optical) eyeglasses with channels, which extend from the ends of the temples to nearby the nose of the user, and which have connections for connecting hoses and a nose piece. The indicated problems can, at least in large part, be resolved. Such glasses, however, have also a number of disadvantages. The channels are difficult to keep clean or cannot be kept clean, and standard tubing and nose pieces cannot be used. The present invention now provides an improved solution that does not have these disadvantages.

The invention provides eyeglasses according to clause 1, an assembly according to clause 11 and a method according to clause 23. By receiving a part of the hose in the receiving space, the hose is at least partly hidden from view, and moreover the part of the hose in question is supported, protected and held in place. It is preferable that also a part of the tubing is received in the receiving space provided for this purpose in the structure. Thus the hose is further hidden from view, and an even larger part of the hose is supported, protected, and held in place. Preferably, the receiving space comprises an open channel. That makes the putting in the relevant part of the hose easy. Preferably an open side of the open channel is facing towards a user's face during use. So, during use the hose is even less visible. An open side of the channel can optionally be sealed by means of first means provided for this purpose. Thus, the part of the hose held securely in the channel is no longer visible. Preferably, a part of the hose is clamped in the receiving space. Thus, the affected part of the hose is even better held in place.

If the eyeglasses comprise a hinge between the structure and a temple, a part of the hose can be guided in the vicinity of the hinge by second means provided for that purpose so as to guarantee a desired minimum bend radius of the part of the hose. Moreover, the second means preferably comprise a plurality of mutually hinged parts, such as in a cable carrier, wherein the mutual hinge angles are limited such that the desired minimum bend radius is guaranteed. That appears to be a practical and effective embodiment. If the eyeglasses comprise a hinge between the structure and a temple, a part of the hose can be guided in the vicinity of the hinge by second means provided for that purpose such that the part of the hose is not, at least not substantially, shortened or extended when the temple and the frame are mutually hinged. So, undesirable kinking, occlusion, and damage to the hose at the location of the hinge are prevented. In addition to that, the second means is preferably a part of the hinge. So, the hinges between the mutually hinged parts may, for example, together further form the hinge between the structure and the temple.

Preferably, the oxygen administration means comprises a tube part which extends at least partially into a nostril of the user during use. Moreover, the tube part is preferably formed by a converted end part of the hose. Thereby the hose is not interrupted and a separate coupling, for example to a separate nose piece, is not needed.

The invention also provides a device as claimed in clause 31. The device is preferably provided with protruding parts suitable for support on a surface. After fitting the eyeglasses in the device, the whole can be laid onto the surface with the protruding parts resting on the surface. For example, the eyeglasses casu quo the lenses are protected during fitting of the hose. If the oxygen administration means further comprise a tube part which, during use, at least partially extends into a nostril of the user, the device preferably comprises third means suitable for mutual positioning of the tube part and the eyeglasses. The third means and thus the mutual position of the tube part and the eyeglasses may be adapted to an individual user.

Clause 1. A first aspect of the present disclosure relates to eyeglasses (1) comprising a structure suitable for holding lenses (4,4') and temples (5,5'), characterized in that a temple is provided with a receiving space (51,51') suitable for receiving a portion (61,61') of a hose (6,6'). In some embodiments, the structure is provided with a receiving space (31,31') suitable for receiving a portion (62,62') of a hose (6,6'). In some embodiments, the receiving space comprises an open channel. In some embodiments, an open side of the open channel is facing towards a user's face during use. In some embodiments, the eyeglasses further comprise first means suitable for sealing an open side of the open channel. In some embodiments, the receiving space is suitable for clamping the part of the hose. In some embodiments, the eyeglasses further comprise a hinge (7,7') between the structure and the temple, characterized in that the eyeglasses are provided with a second means suitable for guiding of a portion {63,63'} of a hose (6,6') in the vicinity of the hinge so as to guarantee a desired minimum bend radius of the part of the hose. In some embodiments, the second means comprise a plurality of mutually hinged parts (8,8'), wherein the mutual hinge angles are limited in such a way that the desired minimum bend radius of the part of the hose is guaranteed. In some embodiments, the eyeglasses further comprise a hinge (7,7') between the structure and the temple, characterized in that the eyeglasses are provided with second means suitable for guiding of a portion {63, 63') of a hose (6,6') in the vicinity of the hinge in such a way that the part of the hose is not shortened or extended when the temple and the frame are mutually hinged. In some embodiments, the second means form part of the hinge.

Clause 11. A further aspect of the present disclosure relates to an assembly of eyeglasses (1) and oxygen administration means (2), the eyeglasses comprising a structure (3) suitable for holding lenses (4,4') and two temples (5,5'), the oxygen administration means comprising a tube (6,6'), characterized in that a part (61,61') of the hose is received in the temple in a receiving space (51,51') provided for that purpose. In some embodiments, a part of the hose (62,62') is received in the frame in a receiving space (31,31') provided for that purpose. In some embodiments, the receiving space comprises an open channel. In some embodiments, an open side of the open channel is facing towards a user's face during use. In some embodiments, an open side of the channels is sealed by means of a first means provided for that purpose. In some embodiments, the part of the hose is clamped in the receiving space. In some embodiments, the eyeglasses further comprise a hinge (7,7') between the structure and the temple, characterized in that the eyeglasses are provided with second means suitable for guiding a part {63,63') of the hose in the vicinity of the hinge so as to guarantee a desired minimum bend radius of the part of the hose. In some embodiments, the second means comprise a plurality of mutually hinged parts (8,8'), wherein mutual hinge angles are limited such that the desired minimum bend radius of the part of the hose is guaranteed. In some embodiments, the eyeglasses further comprise a hinge (7,7') between the structure and the temple, characterized in that the eyeglasses are provided with second means suitable for guiding a part {63,63') of a hose (6,6') in the vicinity of the hinge such that the part of the hose is not shortened or extended when the temple and the structure are mutually hinged. The second means forms part of the hinge. In some embodiments, the oxygen administration means further comprise a tube part (91,91') that extends at least partially into a nostril of a user during use. In some embodiments, the tube part is formed by a converted end part (64,64') of the hose.

Clause 23. Another aspect of the present disclosure relates to a method for building an assembly of eyeglasses (1) and oxygen administration means (2), the eyeglasses comprising a structure (3) suitable for holding lenses (4,4') and two temples (5,5'), the oxygen administration means comprising a hose (6,6'), characterized in that the method comprises putting a portion (61,61') of the hose into the temple in a receiving space (51,51') provided for this purpose. In some embodiments, the method comprises putting a portion (62, 62') of the hose into the structure in a receiving space (31,31') provided for this purpose. In some embodiments, the receiving space comprises an open channel, characterized in that the method comprises sealing an open side of a channel by means of a first means provided for this purpose. In some embodiments, the method comprises clamping the part of the hose in the receiving space. In some embodiments, the eyeglasses further comprise a hinge (7,7') between the structure and the temple, characterized in that the method also comprises, by means of a second means provided for this purpose, guiding a part {63,63'} of the hose in the vicinity of the hinge such that a desired minimum bend radius of the part of the hose is guaranteed. In some embodiments, the eyeglasses further comprise a hinge (7,7') between the structure and the temple, characterized in that the method further comprises, by means of a second means provide for this purpose, guiding a part {63,63'} of the hose in the vicinity of the hinge such that the part of the hose is not shortened or extended when the temple and the structure are mutually hinged. In some embodiments, use is made of a device provided for that purpose suitable for holding the eyeglasses. In some embodiments, the method further comprises, by means of a third means (11) provided for that purpose, mutual positioning of the tube part and the eyeglasses.

Clause 31. Yet another aspect of the present disclosure relates to a device (11) for use in a method for building an assembly of eyeglasses (1) and oxygen administration means (2), the eyeglasses comprising a structure (3) suitable for holding lenses (4,4') and two temples (5,5'), the oxygen administration means comprising a hose (6,6'), wherein the method comprises putting a part (61,61') of the hose into the eyeglasses in a receiving space (51, 51'; 31, 31') provided for that purpose, characterized in that the device is suitable for holding the eyeglasses. In some embodiments, the device is provided at one side with protruding parts (12) suitable for support on a surface. In some embodiments, the oxygen administration means also comprises a tube part (91,91') comprising that, during use, at least partially extends into a nostril of a user, characterized in that the tool comprises third means (11) suitable for mutual positioning of the tube part and the eyeglasses.

An aspect of the present disclosure relates to eyeglasses (1) comprising: a structure (3) suitable for holding lenses (4,4') and temples (5,5'), characterized in that the temples are provided with a receiving space (51,51') suitable for receiving a part (61,61') of a hose (6,6') and a hinge (7,7') between the frame and temple, characterized in that the eyeglasses are provided with a first means suitable for guiding of a part {63, 63'} of a hose (6,6') in the vicinity of the hinge so as to guarantee a desired minimum bend radius of the part of the hose.

A further aspect of the present disclosure relates to eyeglasses (1) comprising: a structure (3) suitable for holding lenses (4,4') and temples (5,5'), characterized in that a temple is provided with a receiving space (51,51') suitable for receiving a part (61,61') of a hose (6,6') and a hinge (7,7') between the frame and temple, characterized in that the eyeglasses are provided with a first means suitable for guiding of a part {63, 63'} of a hose (6,6') in the vicinity of the hinge such that the part of the hose is not shortened or extended when the temple and the frame are mutually hinged.

In some embodiments, the eyeglasses are provided with a first means suitable for guiding of a part {63, 63'} of a hose (6,6') in the vicinity of the hinge so as to guarantee a desired minimum bend radius of the part of the hose and such that the part of the hose is not shortened or extended when the temple and the frame are mutually hinged. For example, the structure may be provided with a receiving space (31,31') suitable for receiving a part (62,62') of a hose (6,6'). The receiving space may comprise an open channel. The open side of the open channel may be facing towards a user's face during use. In certain embodiments, the receiving space is suitable for clamping the part of the hose. In some embodiments, the first means comprises a plurality of hinged parts. For example, the first means may form at least part of the hinge. In some embodiments, the hinge is a flexible hinge comprising a spine and a plurality of ribs. The ribs may be curved. In some embodiments, the open channel is defined in an inner surface of the temples adjacent to the hinge, wherein the open channel transitions to an outer surface of the temples distally from the hinge.

Yet another aspect of the present disclosure relates to eyewear configured for receiving a hose, comprising: a first rim and a second rim; a first temple piece operatively coupled to the first rim; a second temple piece operatively coupled to the second rim; wherein the first temple piece and the second temple piece are operatively coupled to the first rim and the second rim, respectively, by first and second flexible elements each having a spine and a plurality of ribs, and wherein the eyewear comprises a first groove defined in and extending through the first rim, the plurality of ribs of the first flexible element, and the first temple piece, wherein the groove is defined in an inner surface of the first temple piece adjacent the first flexible element, wherein the first groove transitions to an outer surface of the first temple piece distally from the first flexible element, and wherein the eyewear comprises a second groove defined in and extending through the second rim, the plurality of ribs of the second flexible element, and the second temple piece, wherein the groove is defined in an inner surface of the second temple piece adjacent the second flexible element, wherein the second groove transitions to an outer surface of the second temple piece distally from the second flexible element. In some embodiments, the first rim is attached to a first nose pad, and the second rim is attached to a second nose pad, and wherein the groove extends through the first and second nose pad.

In certain embodiments, the first and second flexible elements are each configured to hold a part of a hose in a curve having a minimum bend radius for the part of the hose. The first and second flexible elements may each be configured to hold the part of the hose in a curve having a radius larger than the minimum bend radius for the part of the hose. The first and second flexible elements may each be configured to hold a part of a hose in a fixed position that will not stretch or compress. The groove may be configured to hold a part of the hose in a fixed position that has no longitudinal movement when the first and second flexible elements are bent.

BRIEF DESCRIPTION OF DRAWINGS [FIGURE LEGENDS]

The invention will hereafter be further elucidated on the basis of exemplary embodiments of a pair of eyeglasses, an assembly, and a device according to the invention. In the drawings:

FIG. 12 shows the eyeglasses frame with a standard oxygen hoses in place.

Figure 13A:
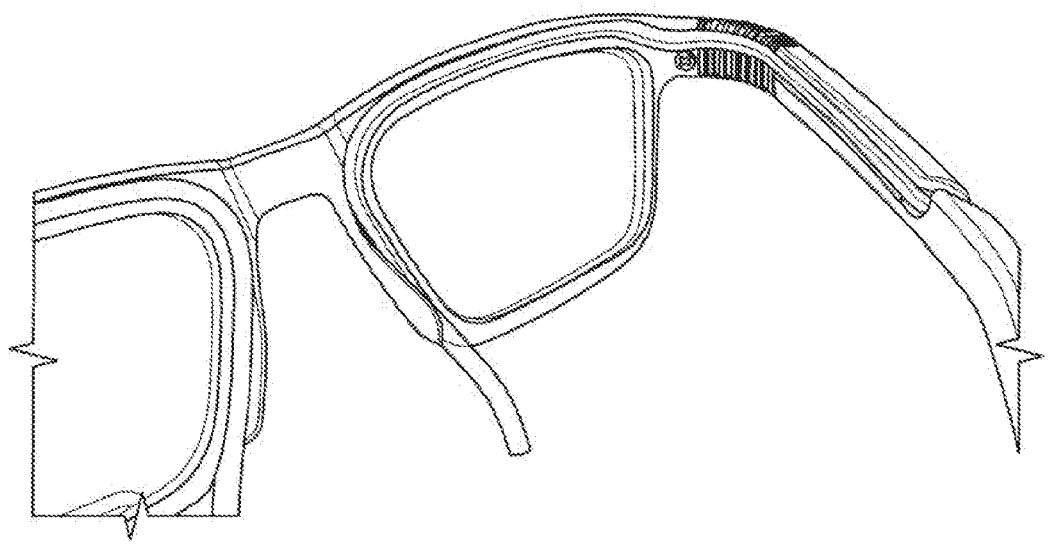
Figure 13B:
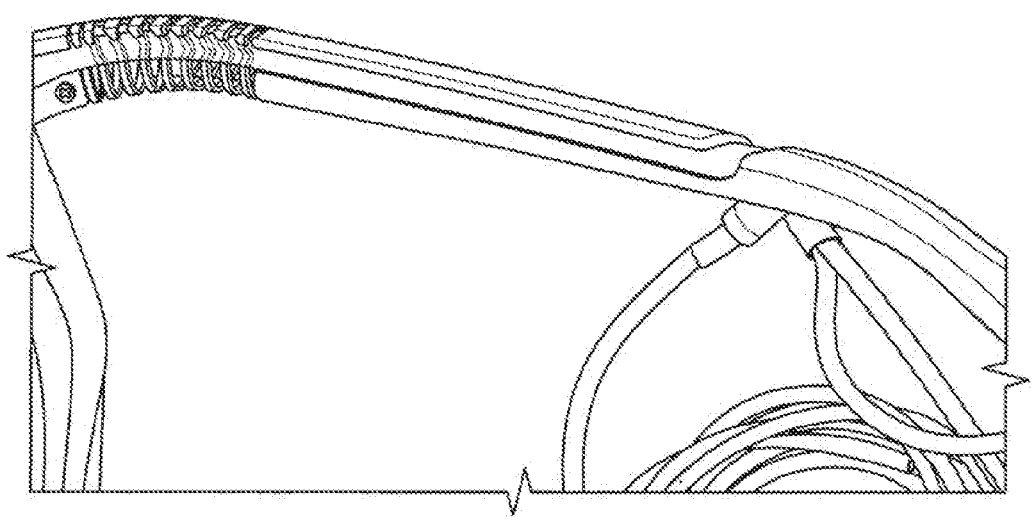
Figure 14A:
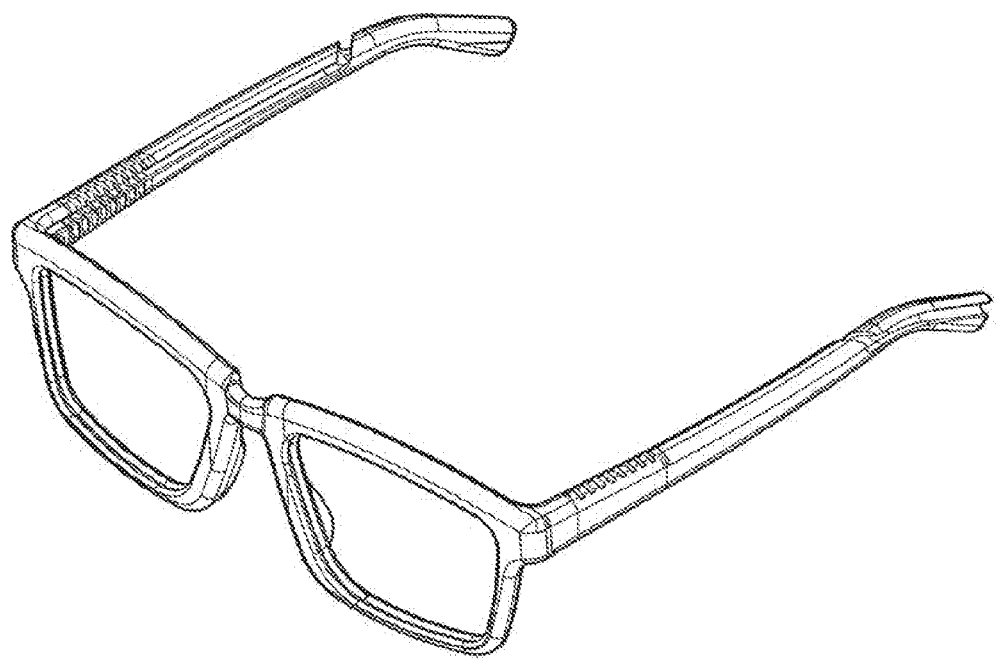
Figure 14B:
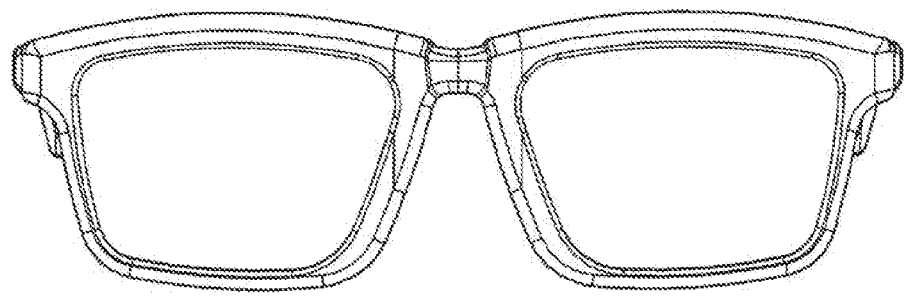
Figure 14C:
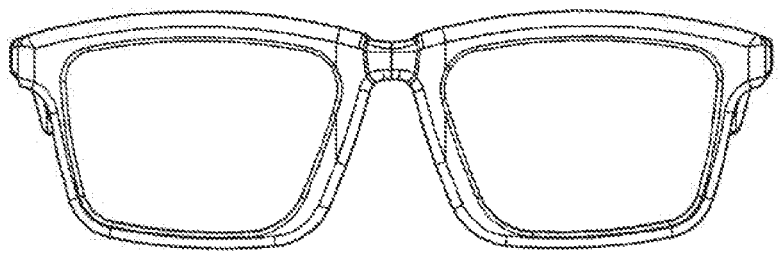
Figure 14D:
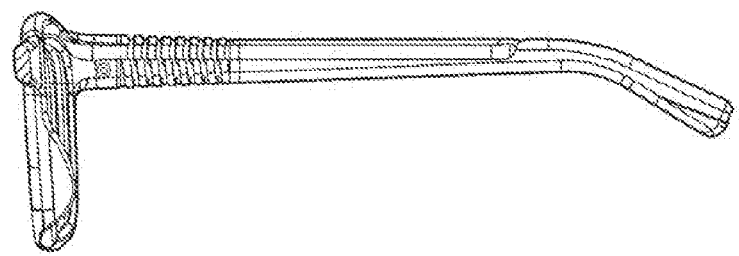
Figure 14E:
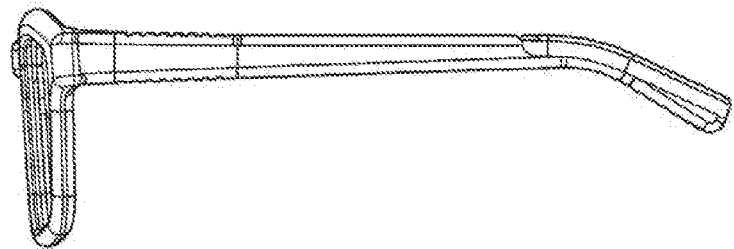
Figure 14F:
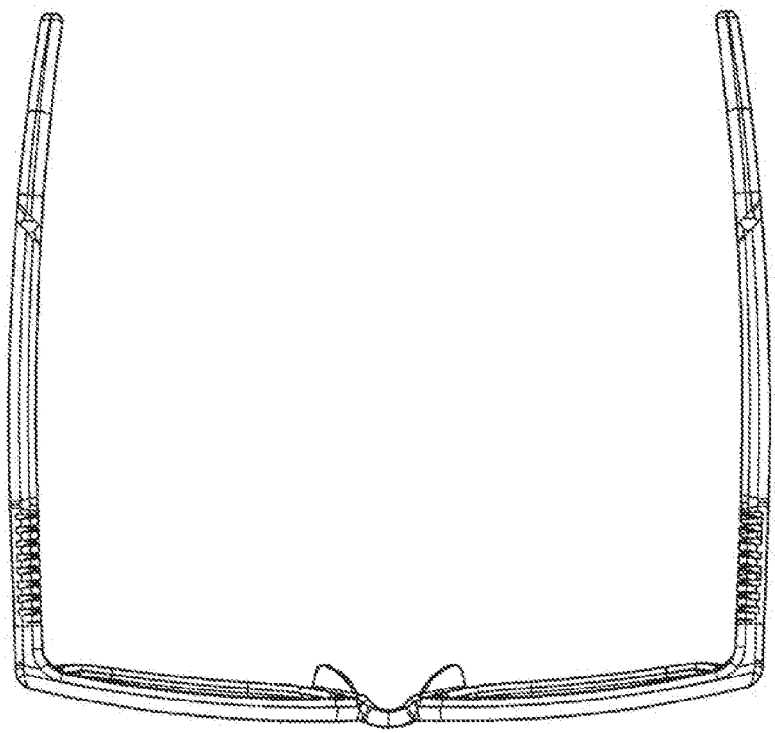
Figure 14G:
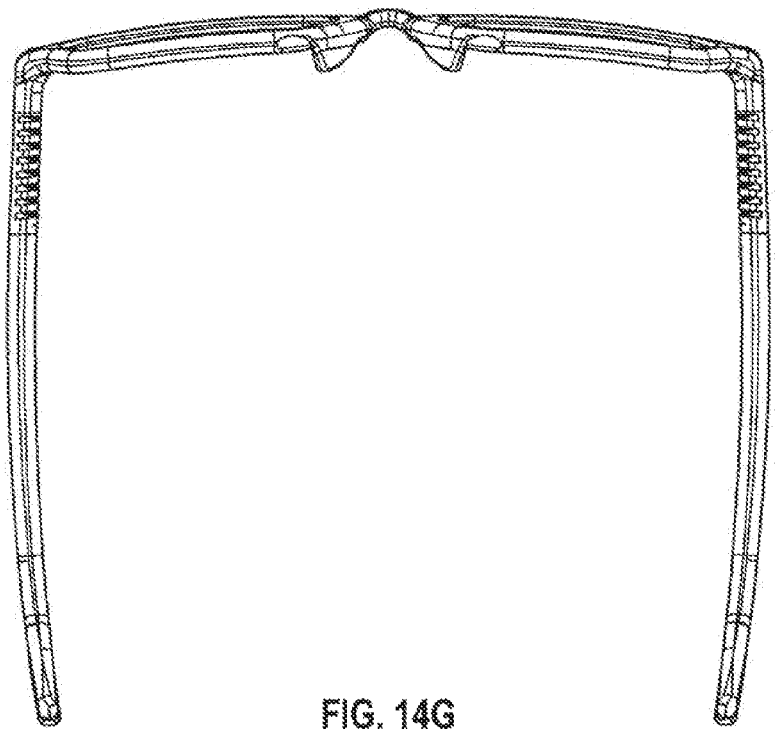
Figure 14H:
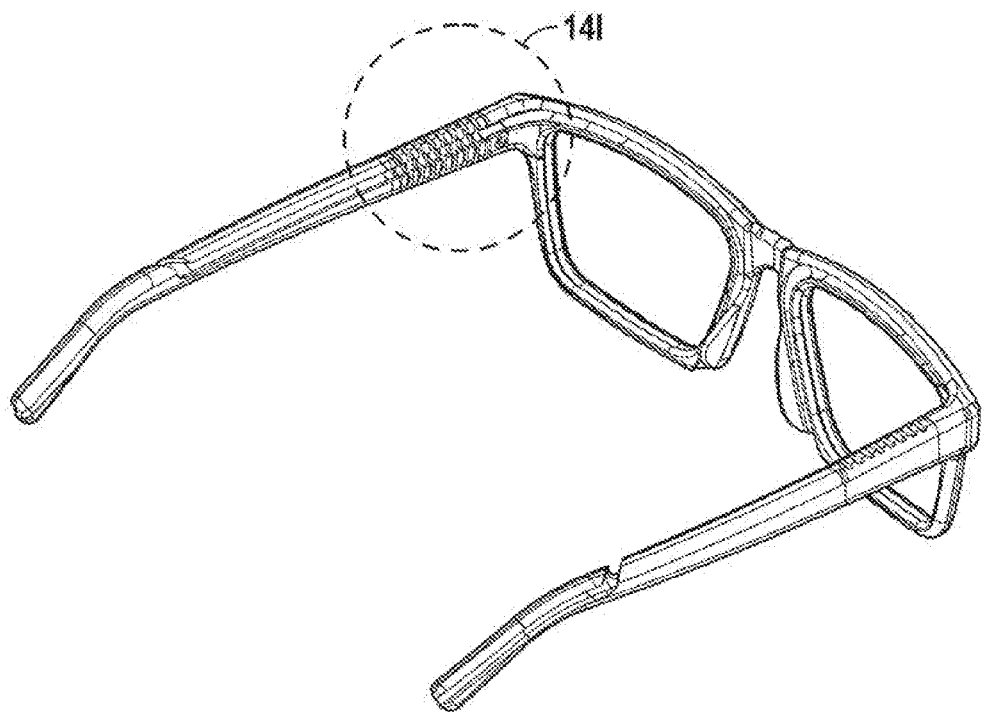
Figure 14I:
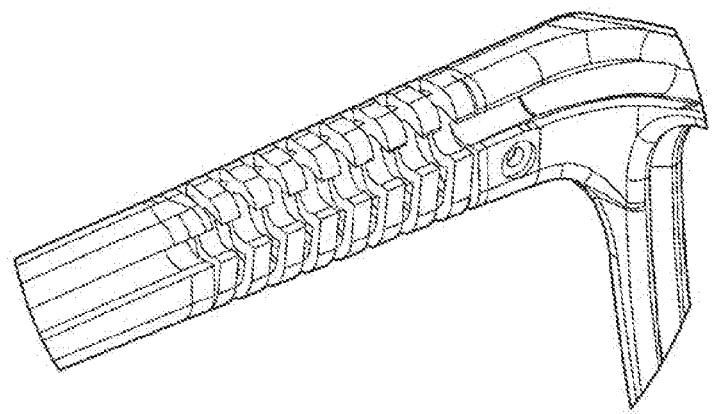
Figure 15A:
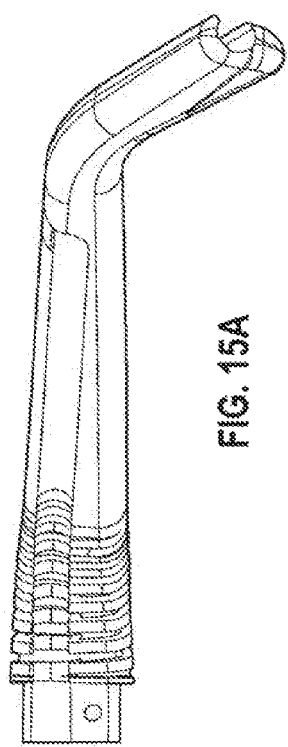
Figure 15B:
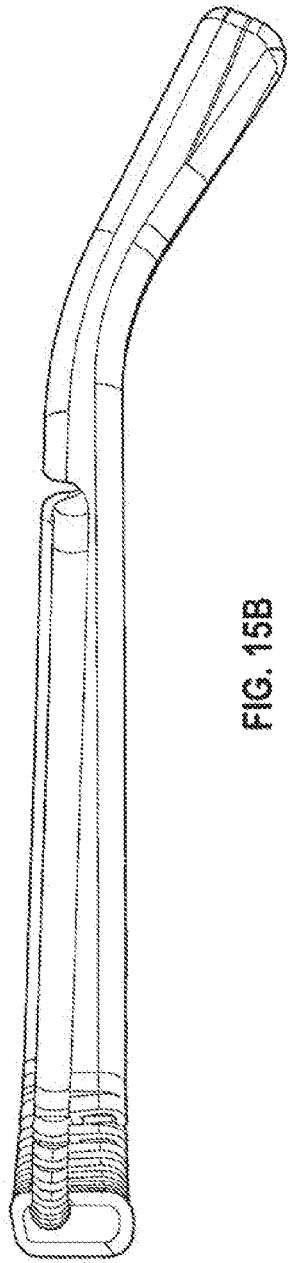
Figure 15C:
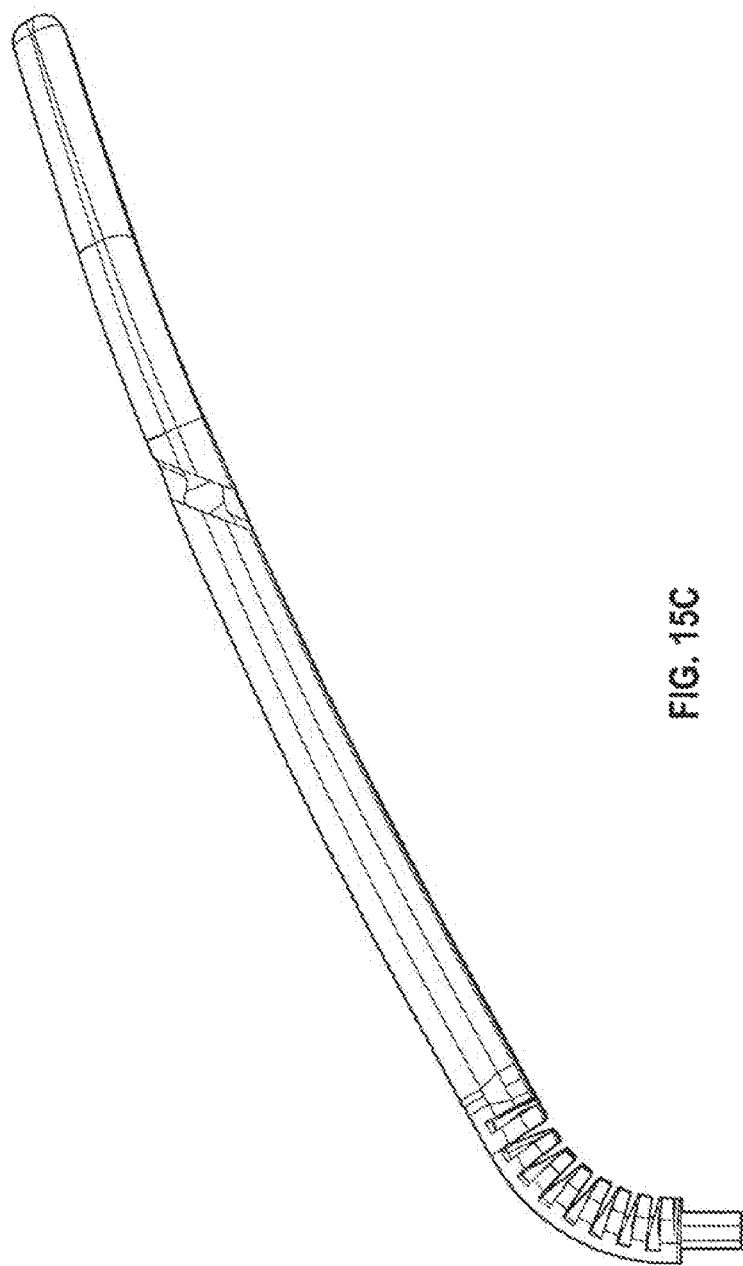
Figures 15D, 15E:
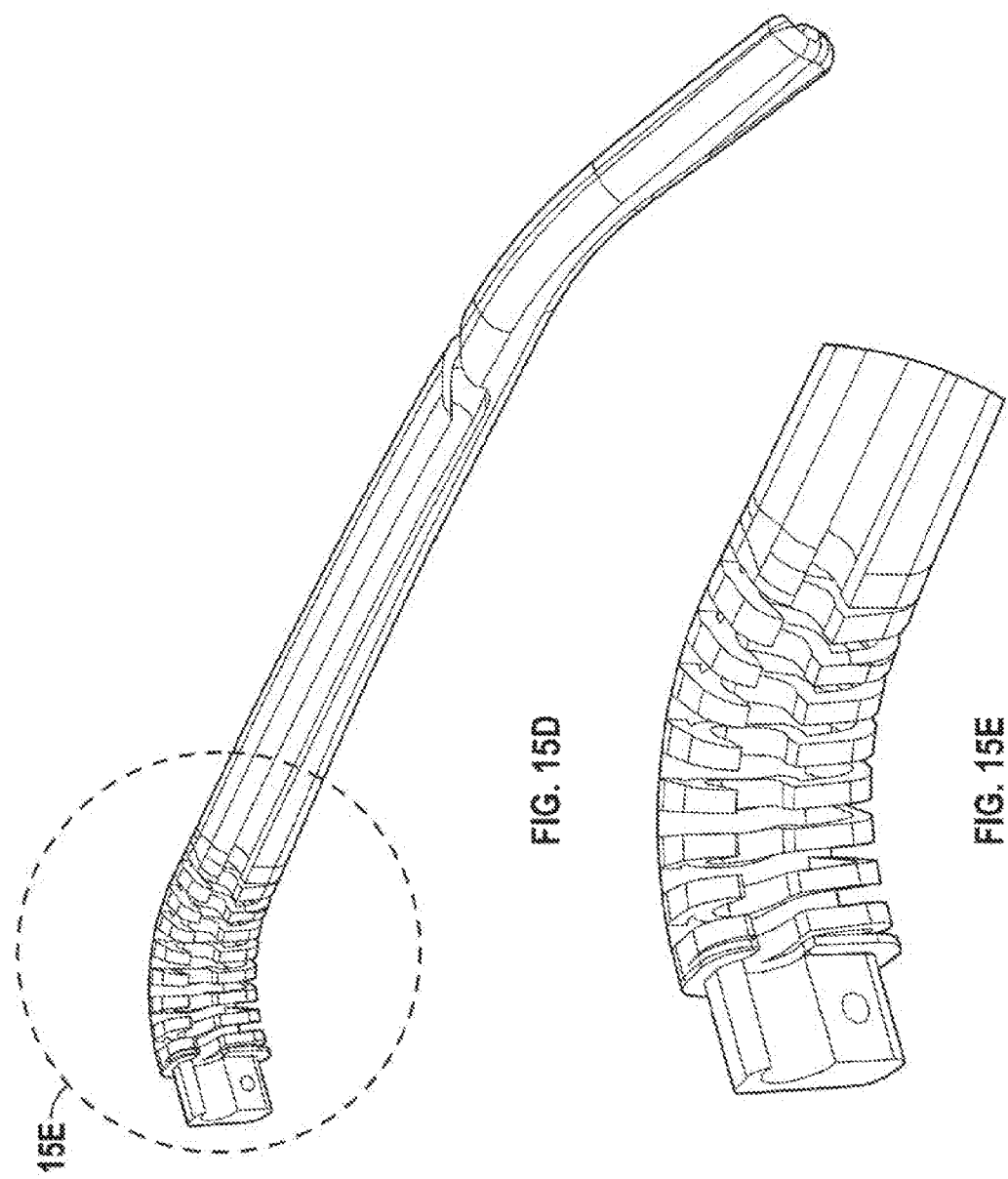

FIG. 13 shows a close-up of the backside of the eyeglasses frame, with the oxygen hose in place. FIG. 13A shows the flexible element (hinge), rim and nose pads, while FIG. 13B shows the flexible element (hinge) and temple. The groove in the temple is located on the inner face of the temple until the temple tips, where the groove is located on the outer face of the temple.

FIG. 14 shows a variety of views of the full-rim eyeglasses frame.

FIG. 15 shows a variety of views of the flexible element (hinge) of the eyeglasses frame.

Figure 16A:
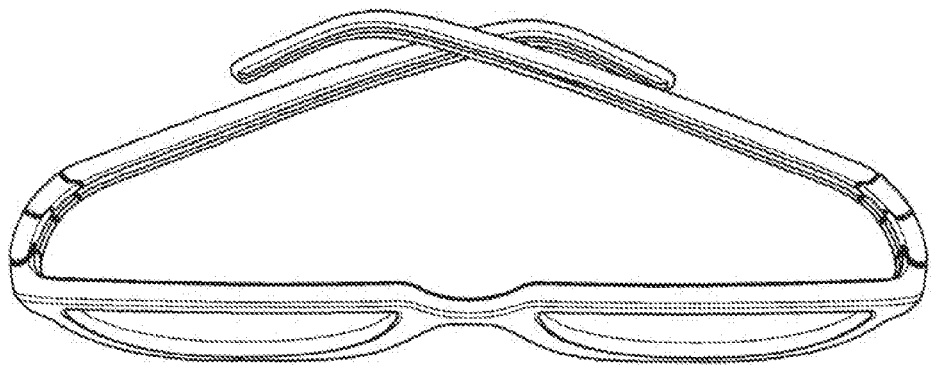
Figure 16B:
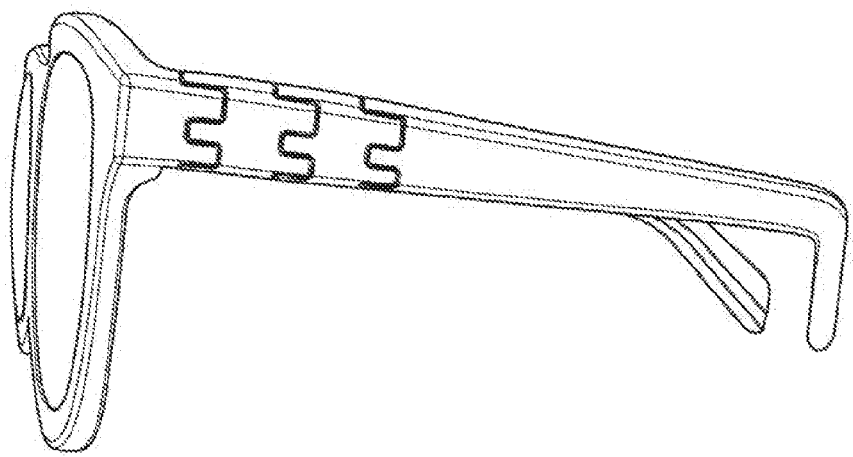

FIG. 16 shows an embodiment of the eyewear, with a flexible element (hinge) having interlocking units.

Figure 17A:
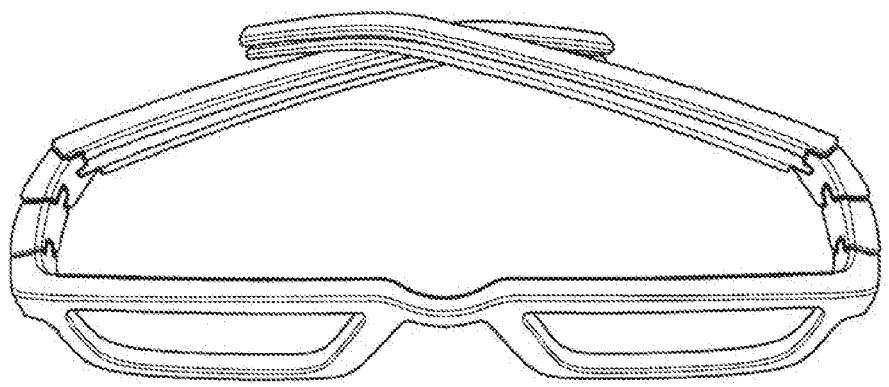
Figure 17B:
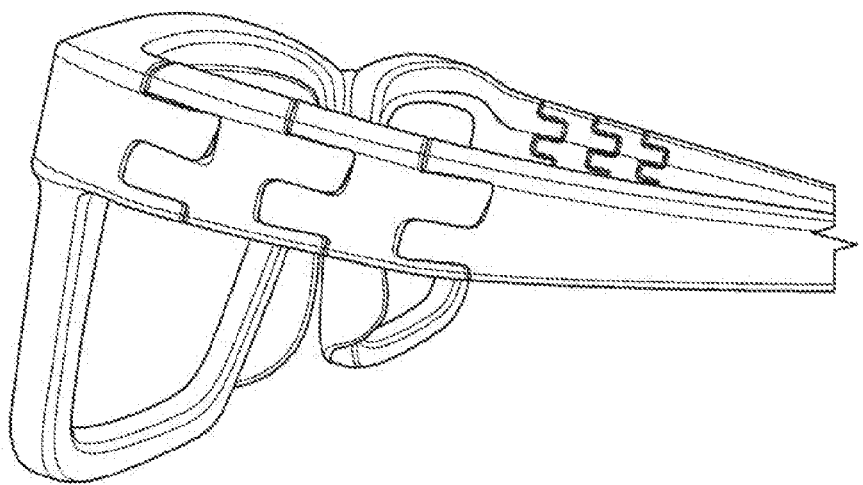
Figure 18A:
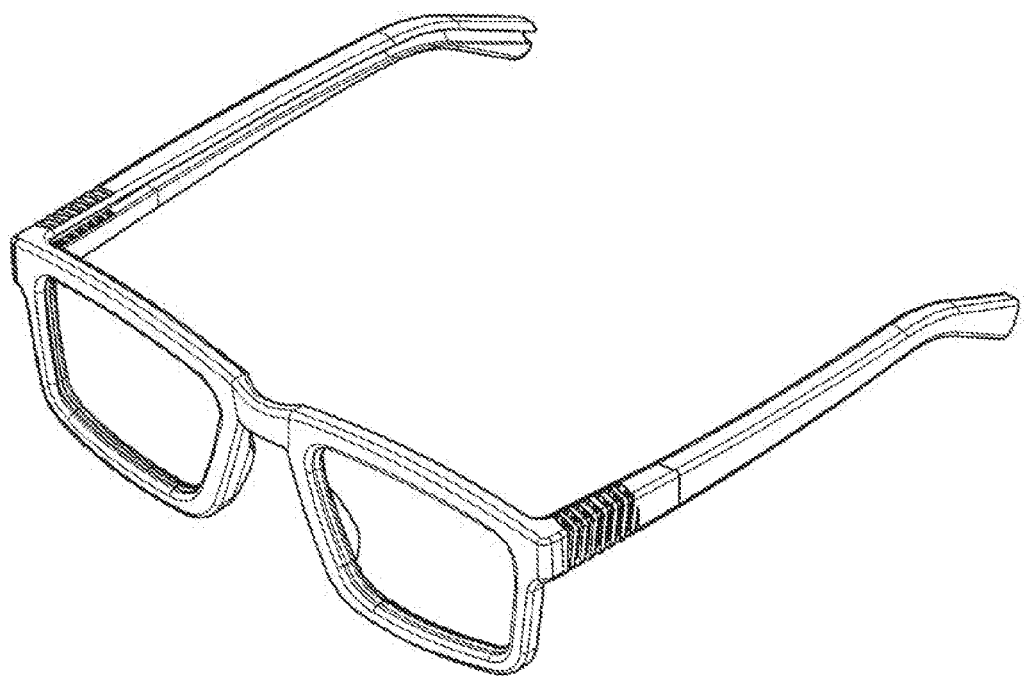
Figure 18B:
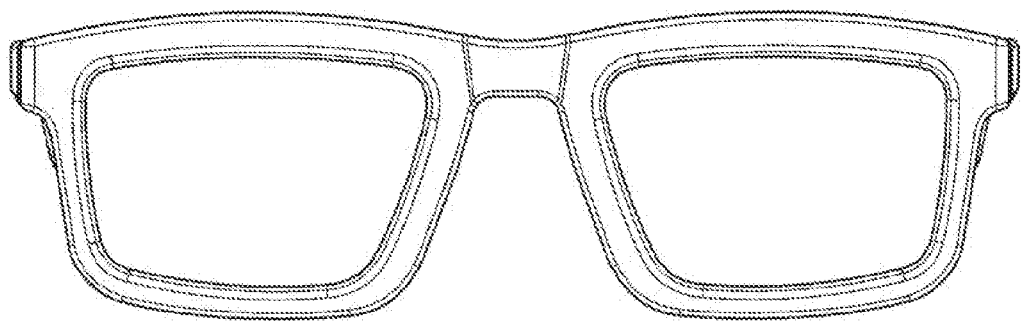
Figure 18C:
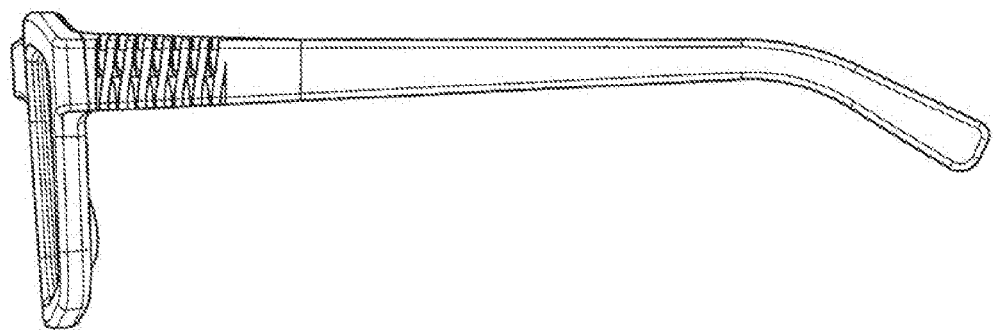
Figure 18D:
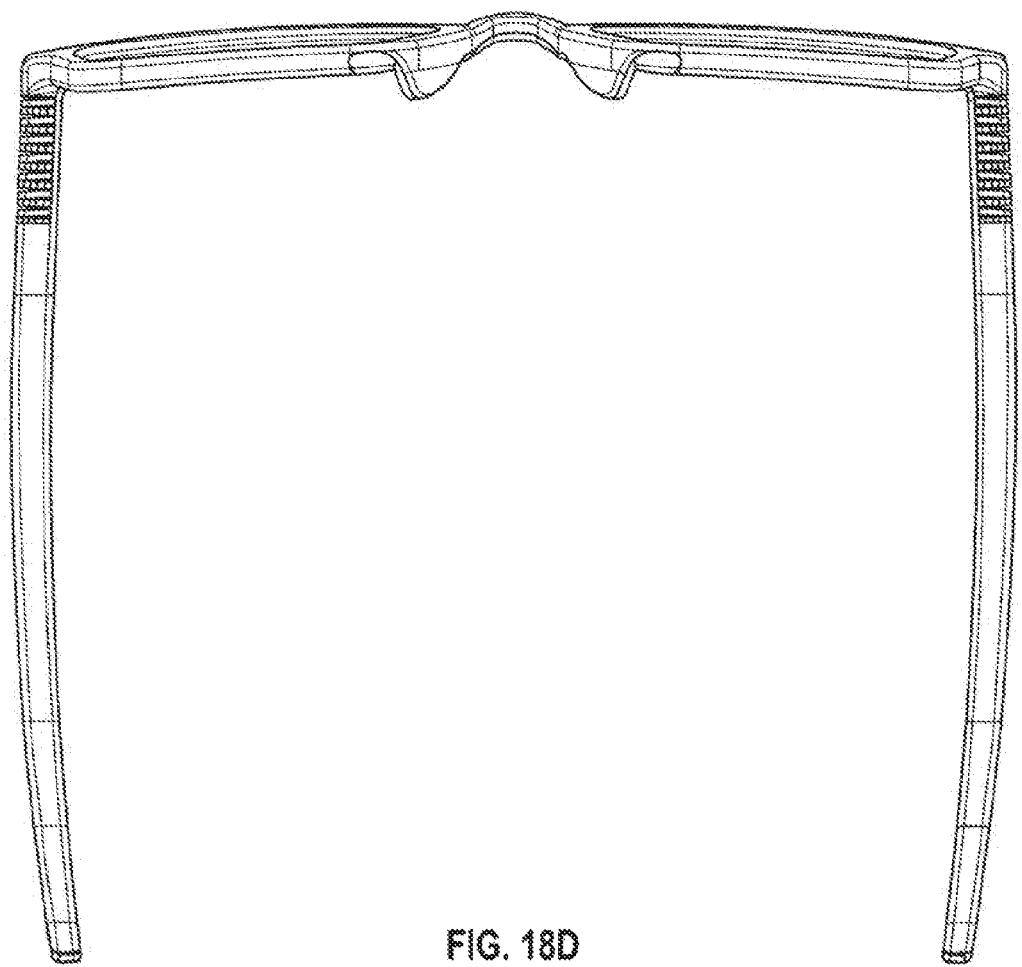
Figure 19A:
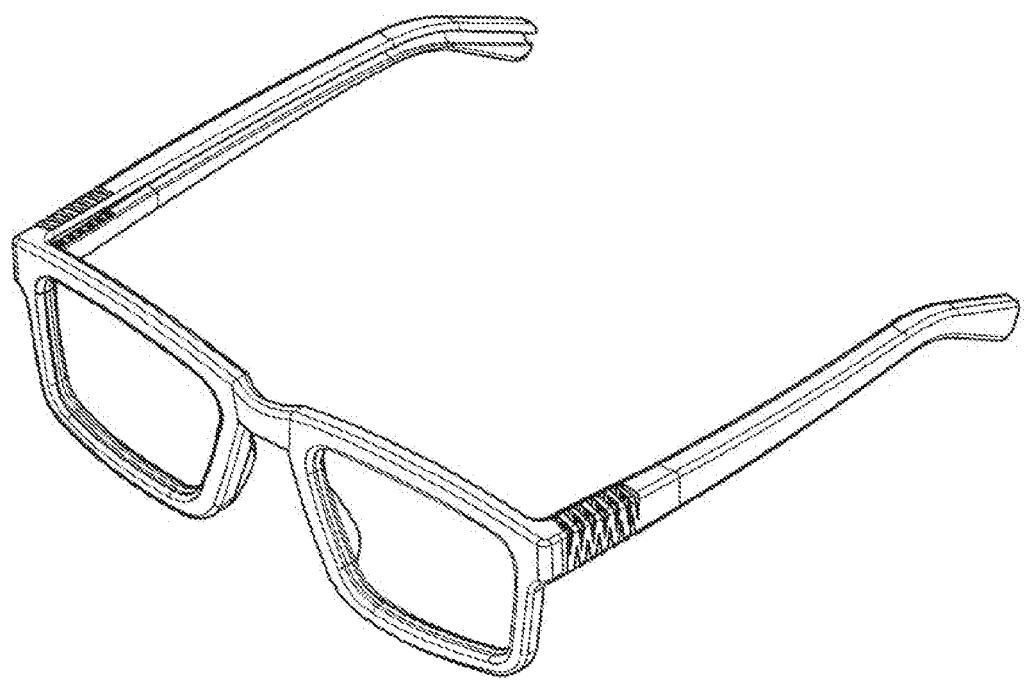
Figure 19B:
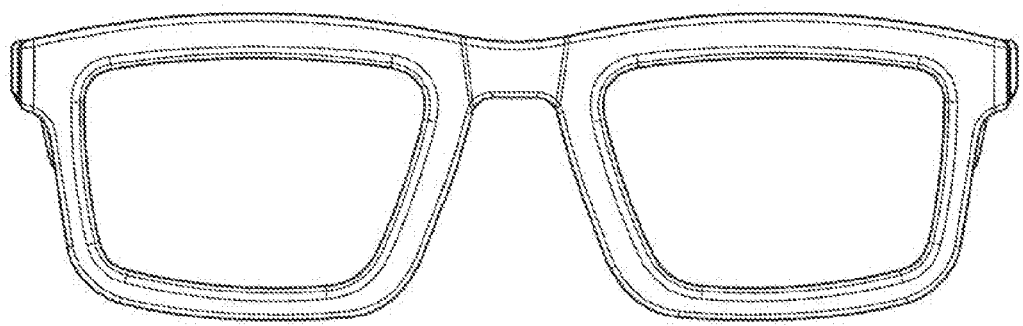
Figure 19C:
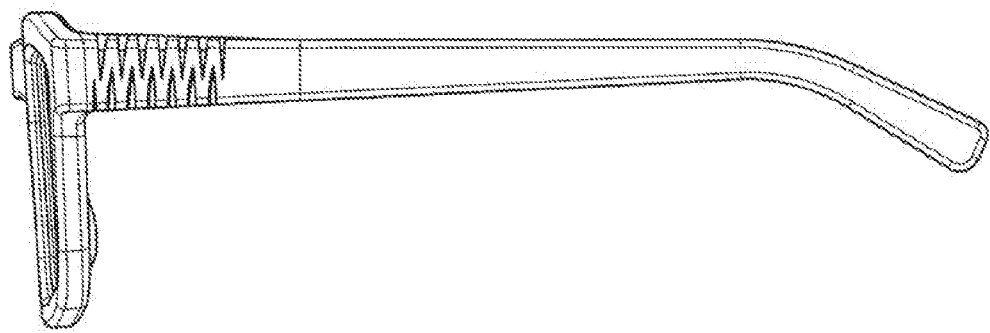
Figure 19D:
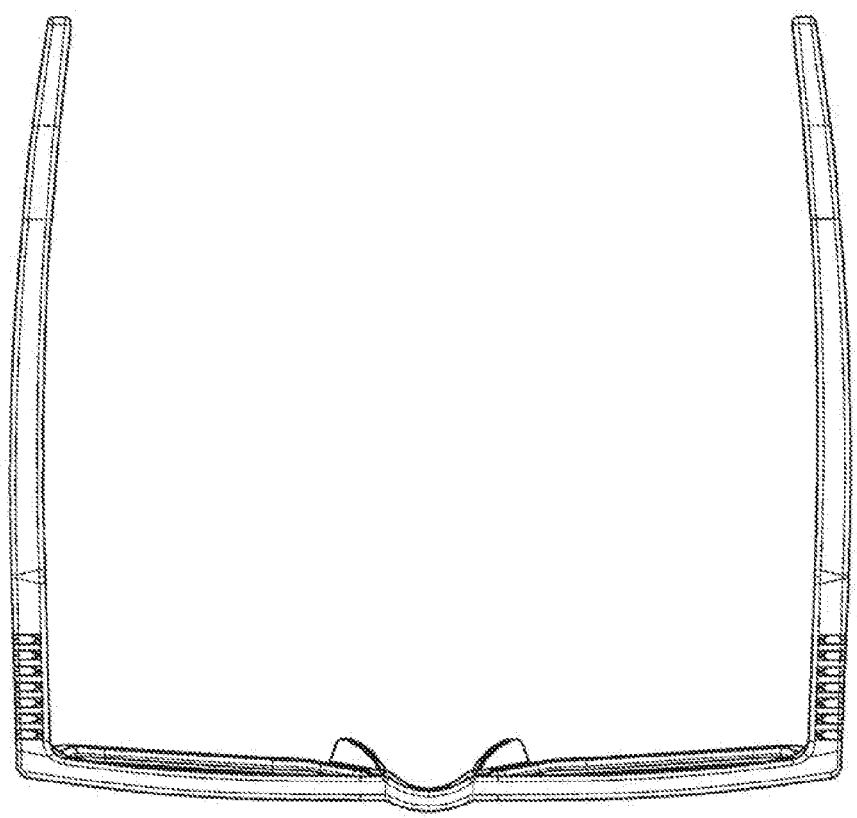
Figure 20A:
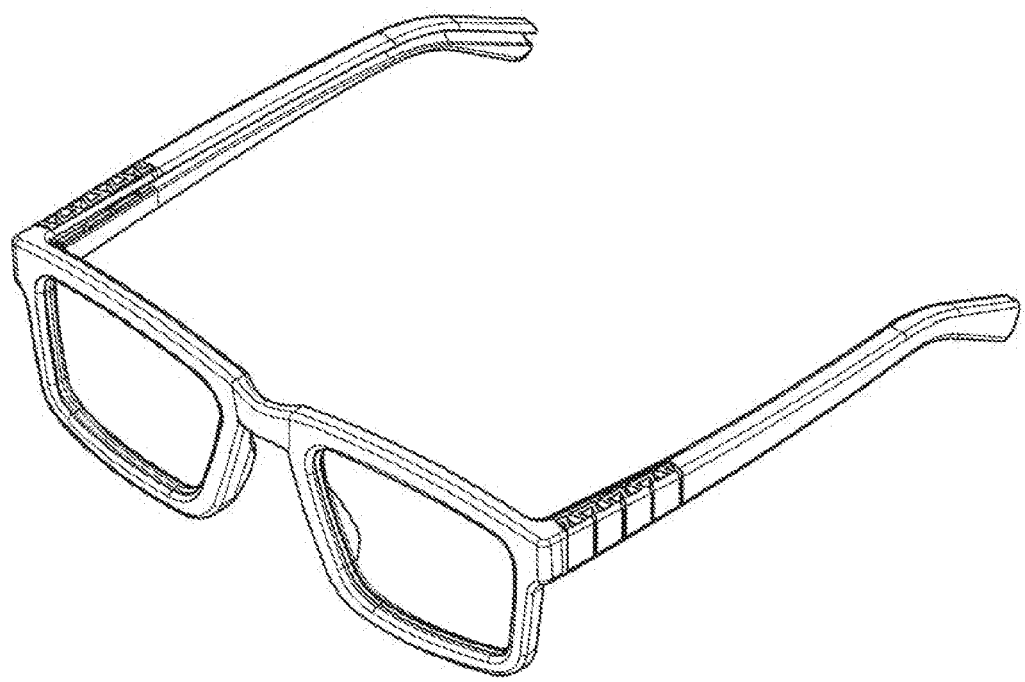
Figure 20B:
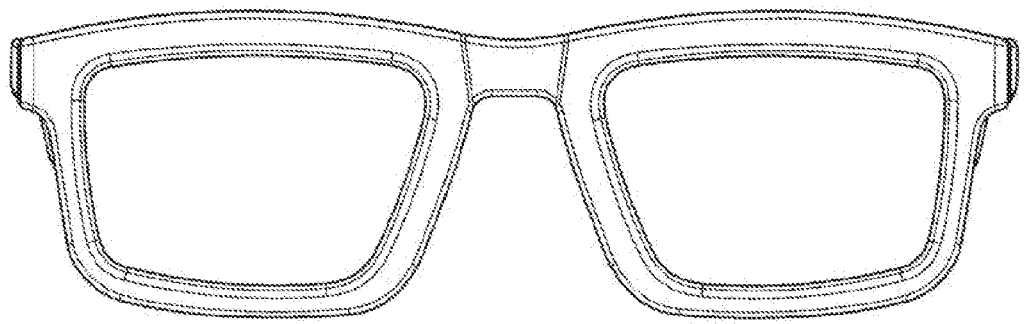
Figure 20C:
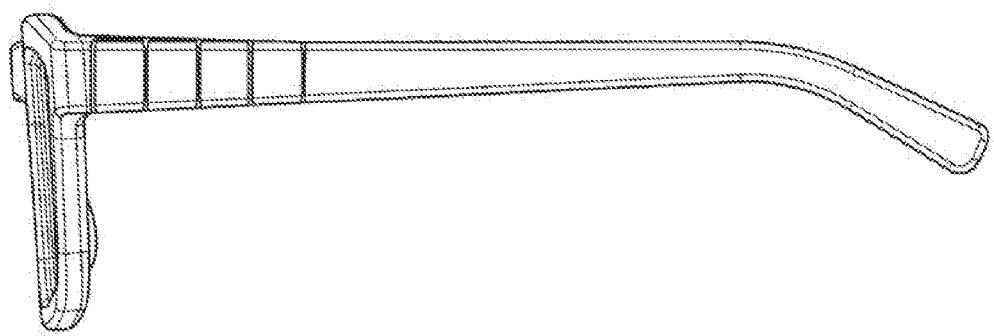
Figure 20D:
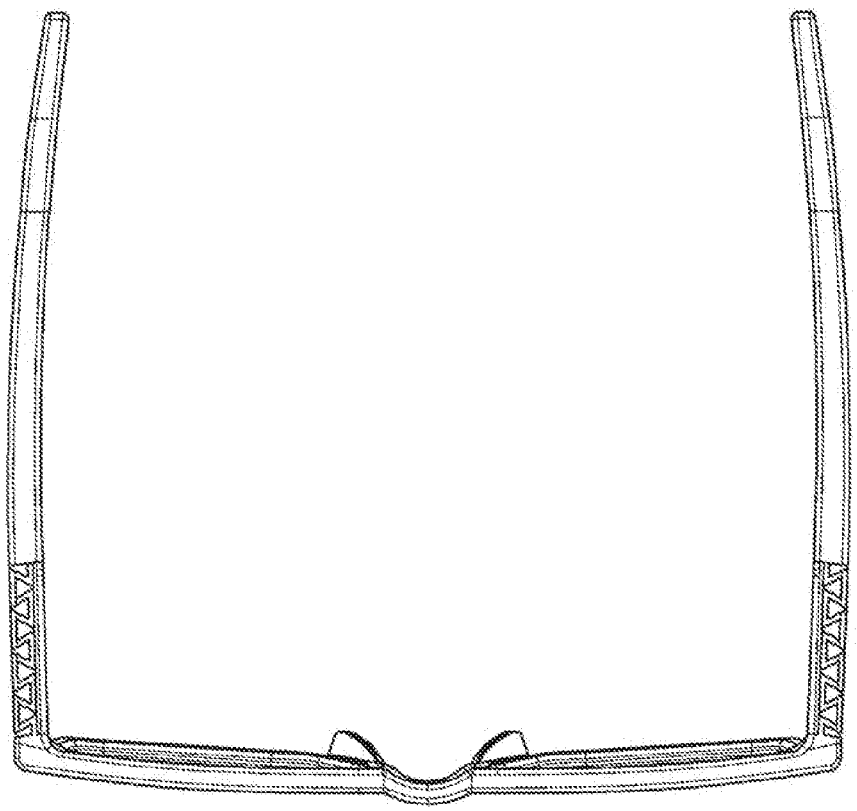
Figure 21A:
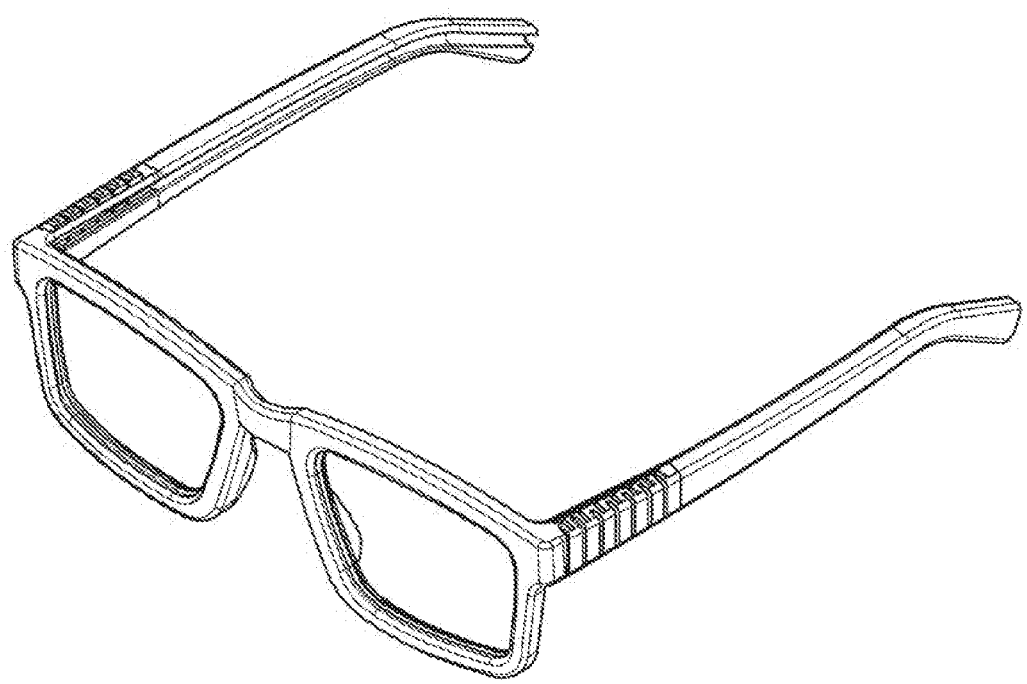
Figure 21B:
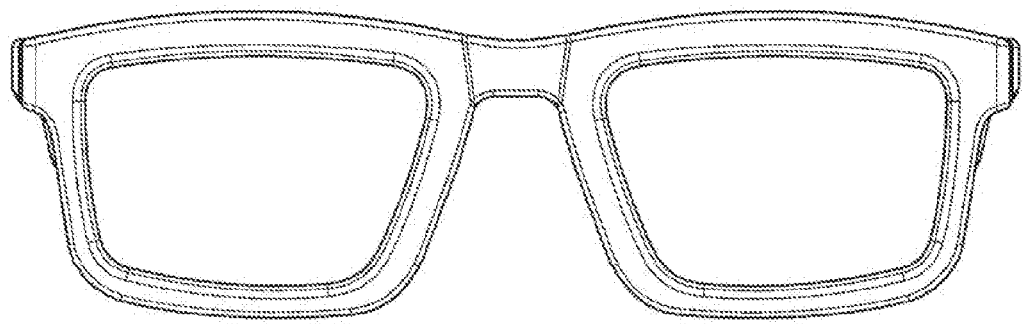
Figure 21C:
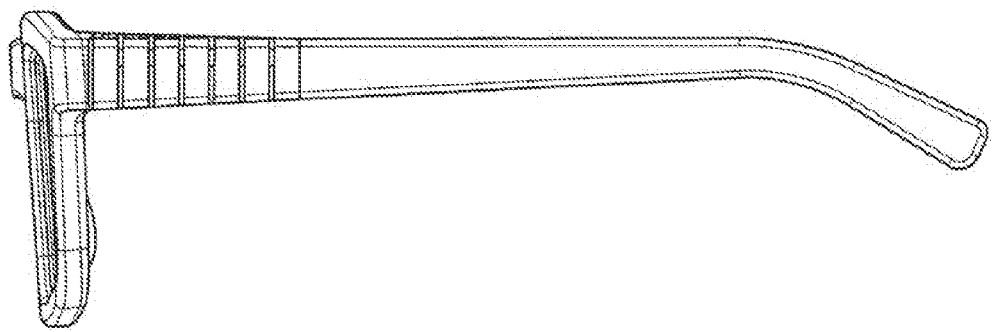
Figure 21D:
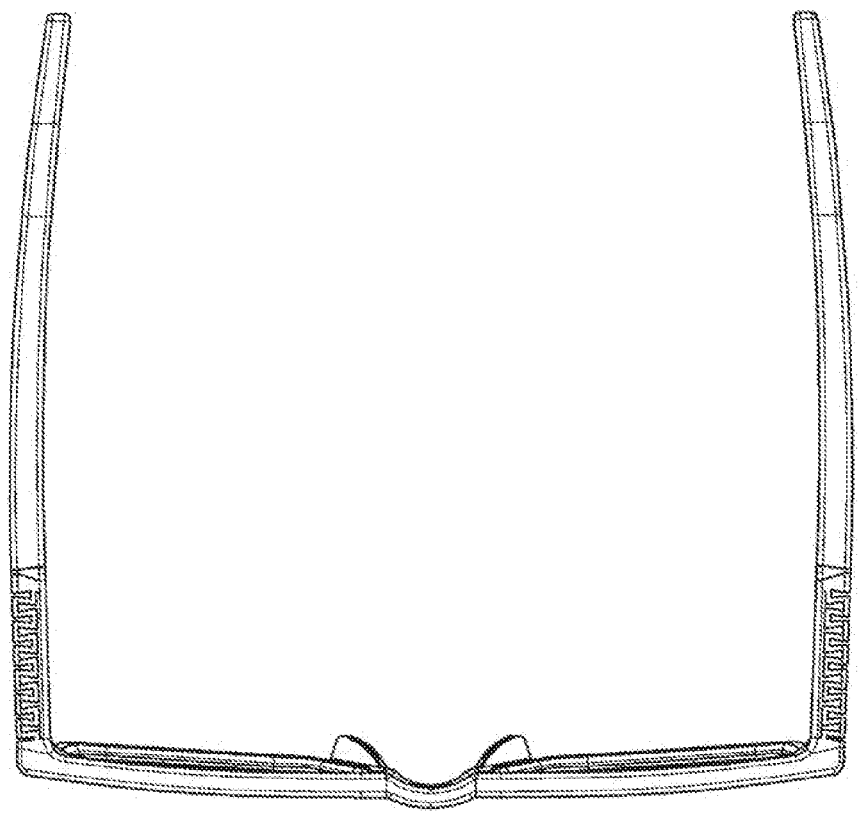

FIG. 17 shows an embodiment of the eyewear, with a flexible element (hinge) having interlocking units and a boxy shape.

FIG. 18 shows an embodiment of the eyewear, with a flexible element (hinge) having a repeating array of angled units.

FIG. 19 shows an embodiment of the eyewear, with a flexible element (hinge) having angled units configured in a zig zag.

FIG. 20 shows an embodiment of the eyewear, with a flexible element (hinge) having an array of repeating triangular units, each joined to its neighboring triangle via a rectangular connection.

FIG. 21 shows an embodiment of the eyewear, with a flexible element (hinge) having an array of Li-shaped units, each joined to its neighboring Li-shaped unit via a rectangular connection.

DETAILED DESCRIPTION OF INVENTION

Medical gas therapy delivery systems, such as the conventional nasal cannula system for oxygen therapy, are often an additional burden to patients who are already suffering from debilitating lung conditions or disorders. The hoses can be uncomfortable, impractical for patients who wear eyeglasses, and unpleasant to wear in social situations. Where possible, patients would prefer an alternative medical gas therapy system that avoids these problems.

One alternative is found in eyeglasses frames that are modified to accommodate, disguise, or even eliminate the parts of the hoses which normally transverse the face and ears in the conventional nasal cannula system. Unlike the conventional nasal cannula hoses, the only visible parts of the oxygen delivery system in the eyeglasses frames are hoses emerging from the temple tips and nasal prongs which lead from the temple tips and nasal prongs from the nose pads of the eyeglasses frame. This is a discreet and comfortable option for most patients, and is an especially natural fit for those patients who wear eyeglasses for vision correction. This eyewear may be used to enhance the performance and usability of oxygen administration means, particularly the hoses used in oxygen therapy. The eyewear may be used with hoses that attach to any oxygen source, such as devices like gas tanks, liquid oxygen tanks which are either reservoirs or portable canisters, oxygen concentrators that are either stationary or portable, or home fill systems.

Early Eyewear Designs

Over the years, a variety of oxygen delivery eyewear systems have been developed. For example, eyeglasses frames may be hollowed so that oxygen flows through a hollow channel in the eyeglasses temples, frames and nose pads of the eyeglasses, and exits into nasal tubes that lie along the sides of the patient's nose. In U.S. Pat. No. 5,193,534, the eyeglasses have a hollow shell framework through which the oxygen passes, either from a double or single attachment of a source tube to the ends of the temple ear pieces. U.S. Pat. No. 6,886,562 and US20080257343 expand on the hollow eyeglasses frames, either by introducing a folding mechanism that prevents deformation of common joint portions of spectacles (U.S. Pat. No. 6,886,562) or by creating a hingeless design (US20080257343). While it is convenient to use eyeglasses frames for oxygen delivery, the hollow channel design has a few disadvantages compared to using hoses. For some models with hinges that fold and open, the air in the channels can become contaminated with pollutants or pathogens that are then delivered directly to the patient's nose and lungs. For all models, the hollow channels are difficult to clean and inconvenient to replace. Because the hollow eyeglasses frames have channels which effectively replace the need for portions of the tubing, it is not possible to use standard tubing for those portions, even though it may be desirable to select tubing having a known material, size, diameter, wall-thickness, or known flow properties. Patients would have to exchange their eyeglasses frames for entirely new frames if they wanted to change the hollow channels, assuming that alternative sizes or materials of the hollow channel eyewear frames were even available.

Figure 9:
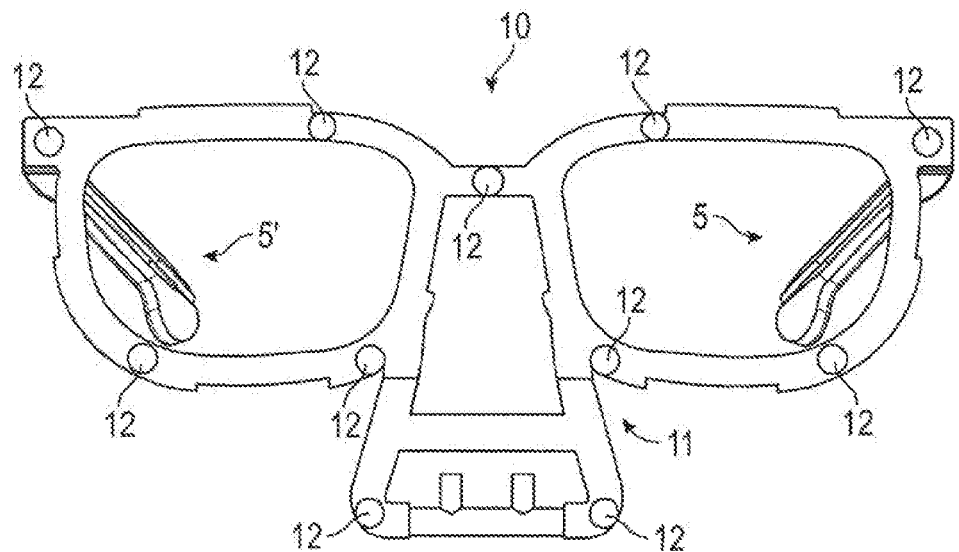
FIG. 9 is a front view of a device according to the invention with the glasses.

In another design, eyeglasses frames are modified to accommodate standard oxygen hosing. U.S. Pat. No. 4,559,941 discloses an eyeglasses frame having grooves in the rear surface and groove in the interior surface of each of its hinged temples to fit a cannula assembly. In FIG. 9 of U.S. Pat. No. 5,193,534, there is an alternative embodiment of the hollow shell frame in which the hose is affixed to the eyeglasses frame. In WO8703704A1, a hose is clipped to the eyeglasses frame. A design in CA2125790C has not only grooves in the left and right arms of the eyewear frame and in the back of the face member of the eyewear frame to accommodate an oxygen nasal cannula but also a face plate configured to cover the cannula groove during use and arm plates to cover the cannula grooves in the arms. DE202014006155U1 shows an eyewear frame design having grooves in temple and back face of glasses.

While the modified eyewear frames offer more flexibility than the hollow channel designs, none of the existing frames have been specifically designed to accommodate the natural movement and bending of the oxygen hose. Hoses are typically made from plastic, vinyl such as PVC or silicone, and are slippery. Hoses should be flexible enough and have a suitable wall thickness for bending, but must not be easily pulled, kinked, twisted, or folded in such a way as to obstruct oxygen flow or damage the hose. Thus, when hoses are clipped to an eyeglasses frame or pressed into a groove on the eyeglasses frame, it is also critical to ensure that the hoses are not pinched by hinges or forced along a winding path that could introduce kinks or twists, or cause damage by stretching and compressing the hose. In addition, the hoses must be securely attached in all directions in order to prevent the hose from becoming disengaged from the eyeglasses frame, or from stretching and/or sliding longitudinally out of its groove or channel. There remains a need in the art for eyewear configured to accommodate standard hoses for medical gas therapy and configured to bend with the hoses in a flexible but controlled manner. Such eyewear should allow a substantially uninterrupted flow of gas, for example, by guaranteeing that the hose would not bend into a curve having a radius smaller than its minimum bend radius.

Figure 1:
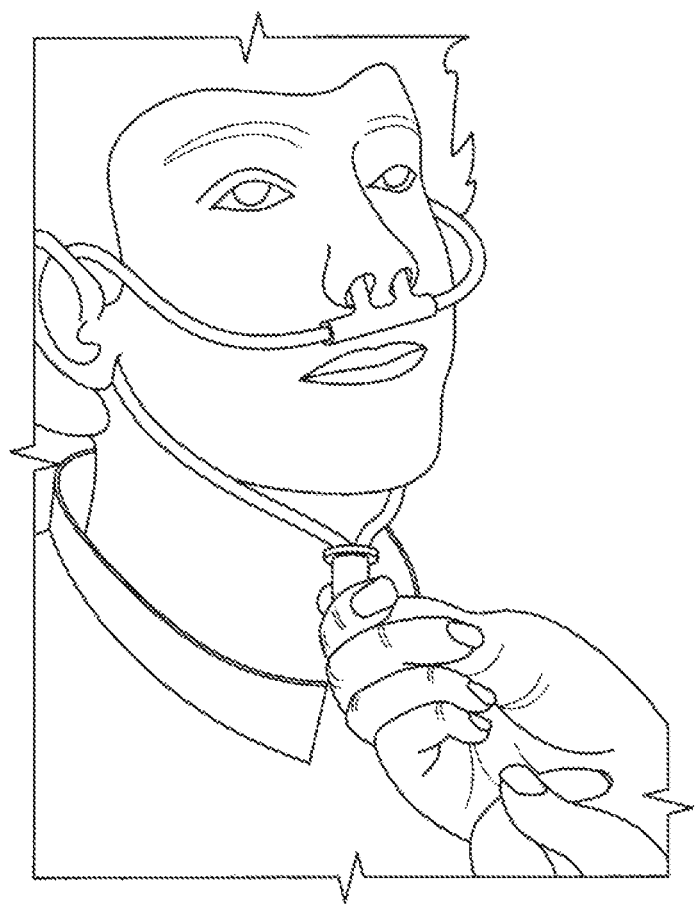
FIG. 1 shows a nasal cannula according to the prior art.
Figure 2:
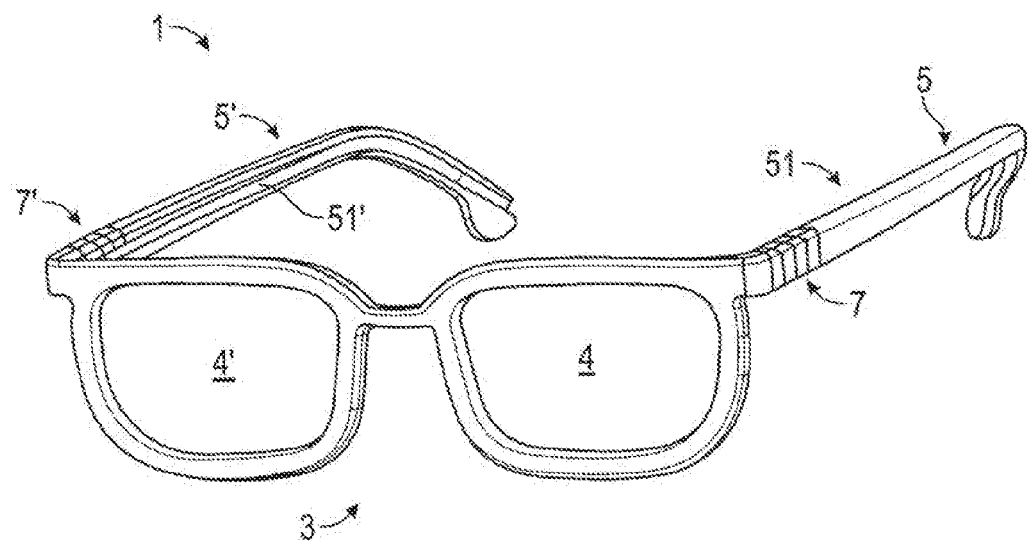
FIG. 2 is a perspective front view of eyeglasses according to the invention.
Figure 3:
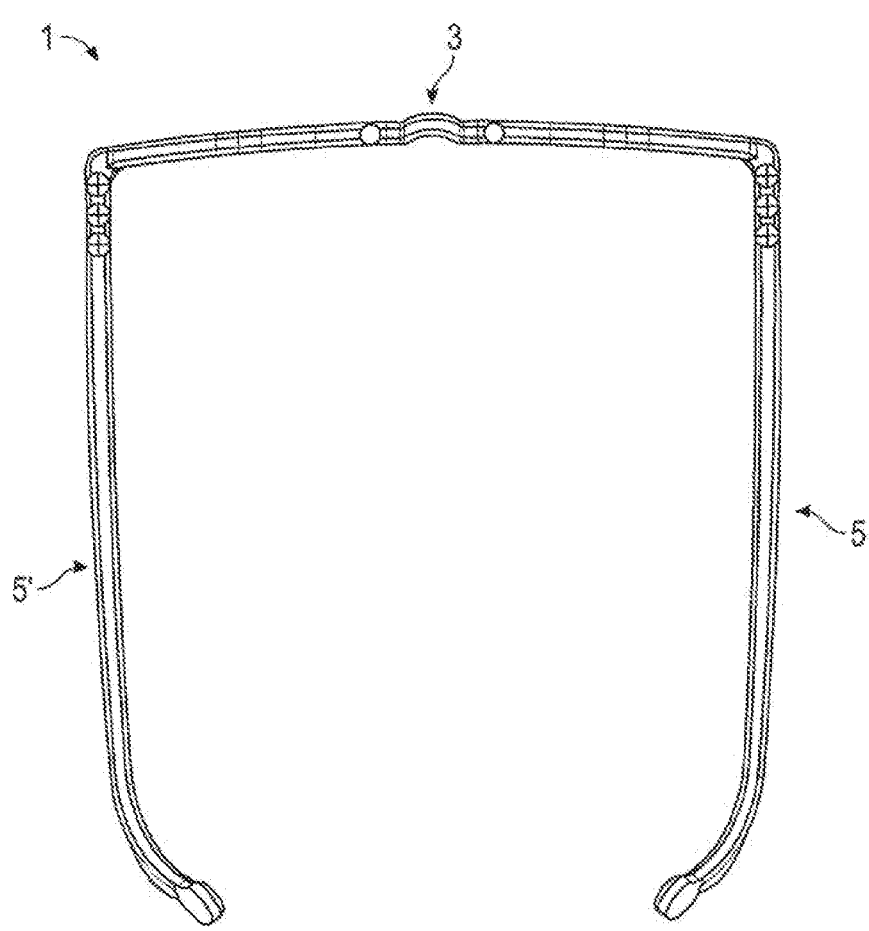
FIG. 3 is a bottom plan view thereof.

Exemplary Eyeglasses, Assembly of Eyeglasses and Oxygen Administration Means, and a Device FIG. 1 shows a nasal cannula or oxygen eyeglasses according to the prior art. In particular, the current parts of the tubes and the nose piece along the face are striking and disturbingly visible. Also, mentioned parts can slide from their place or leave marks on the face. In particular, the parts of the hoses extending along behind the ears interfere with the wearing of (optical) eyeglasses.

Figure 4:
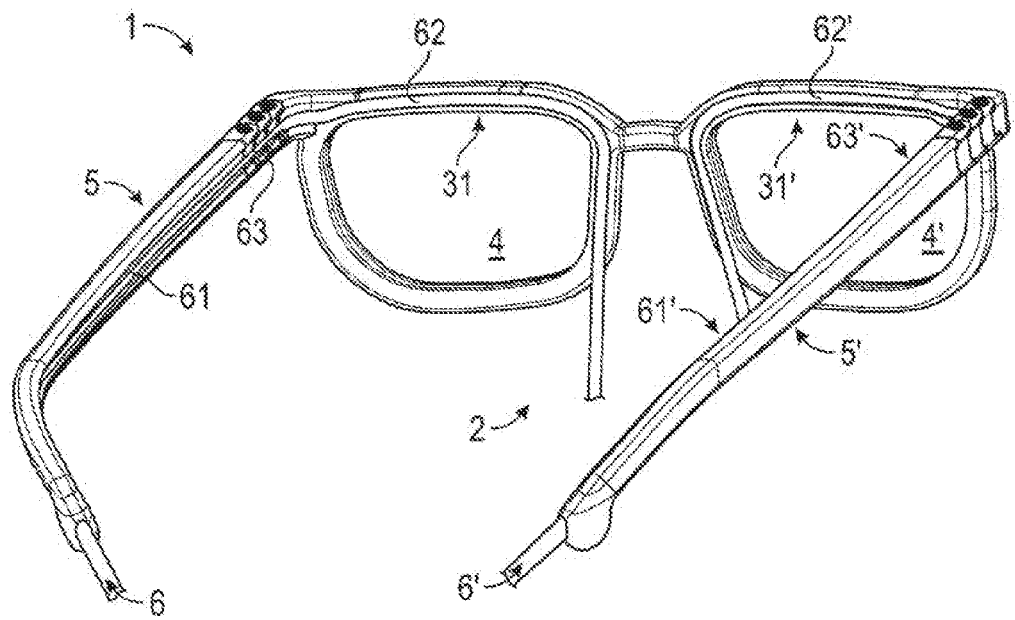
FIG. 4 is perspective rear view of a part of an assembly according to the invention.
Figure 5:
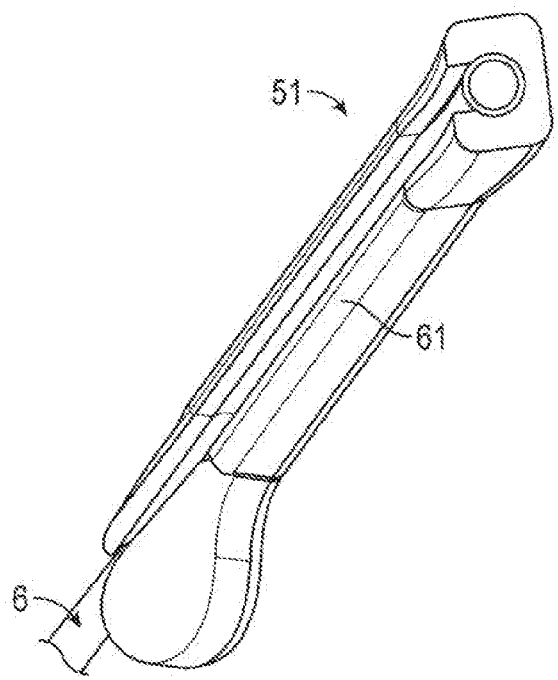
FIG. 5 is a perspective view of a detail thereof.
Figure 8:
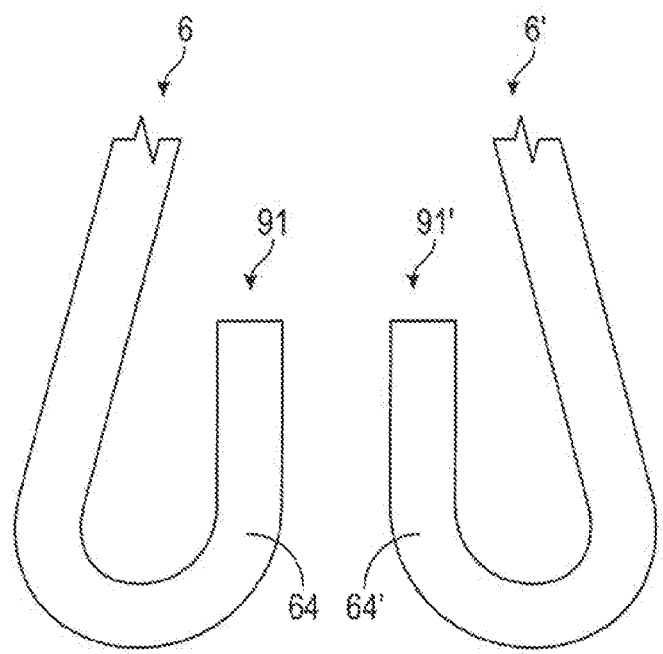
FIG. 8 is a front view of a detail of the assembly.

FIGS. 2, 3, 6 and 7 show an embodiment (1) of a pair of eyeglasses according to the invention. FIGS. 4, 5 and 8 show an embodiment according to the invention of an assembly of such a pair of eyeglasses (1), and oxygen administration means (2) which comprises two tubes (6,6'). The eyewear (1) comprises, as is customary, a structure (3) for holding two lenses (4,4') and two legs or temples (5,5'). Each temple (5,5') is here provided with a receiving space (51,51') for receiving a part (61,61') of one of the two hoses (6,6'). Further, the structure (3) here is also provided with two receiving spaces (31,31'), each suitable for receiving a part (62,62') of one of the two hoses. Each receiving space (51,51'; 31,31') comprises an open channel having an open side which is facing, during use, towards the face of the user. Said parts (61,61'; 62,62') of the hoses (6,6') can be clamped into the relevant receiving spaces (51,51'; 31,31').

Each temple (5,5') is connected to the structure (3) by means of a hinge (7,7'). Each hinge (7,7') comprises mutually hinged parts (8,8'), similar to a cable carrier. The mutually hinged parts (8,8') guide the parts {63,63'} of the two hoses (6,6') in the vicinity of the hinges (7,7'), and in such a manner that a desired minimum bend radius of the parts {63,63'} of the two pipes (6,6') is guaranteed, to which the parts {63,63'} of the two hoses (6,6') along the mutually hinged parts (8,8') run, and the hinge angles between the mutually hinging parts (8,8') are limited. Further the mutually hinged parts (8,8') also guide the parts {63,63'} of the two pipes (6,6') such that the parts {63,63'} of the two pipes (6,6') are not, at least not substantially, shortened or extended when the temple (5,5') and the structure (3) are mutually hinged, where the hinge axes of the mutually hinged parts (8,8') intersect the parts {63,63'} of the two hoses (6,6') running through the mutually hinged parts.

Figure 10:
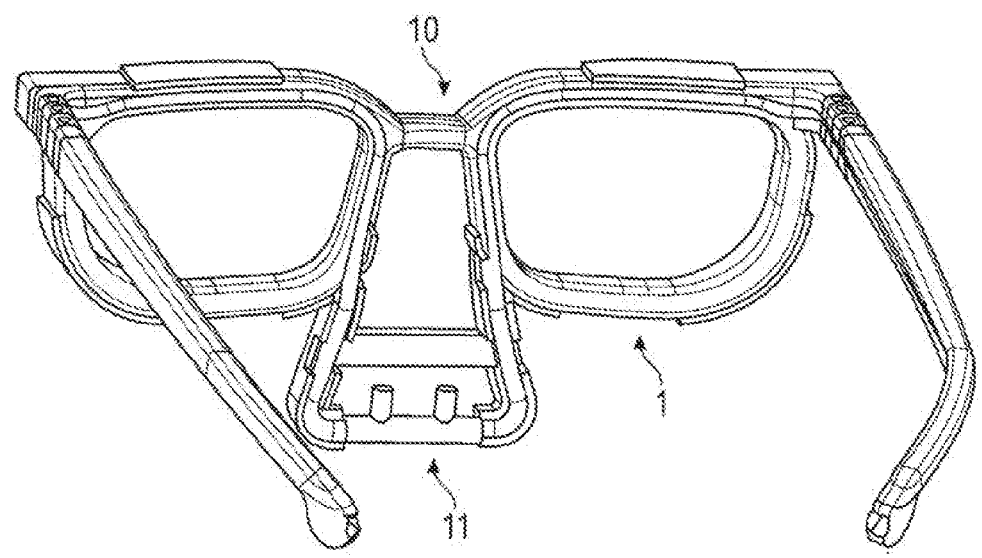
FIG. 10 is a rear perspective view thereof.
Figure 11A:
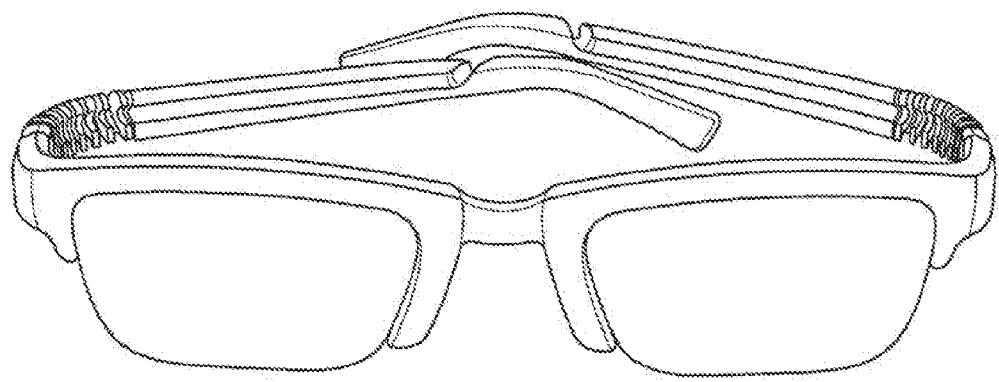
FIG. 11 shows a half-rim style of eyeglasses frame (FIG. 11A, front view and FIG. 11B, back view) and a full-rim style of eyeglasses frame (FIG. 11C, front view and FIG. 11D, back view).
Figure 11B:
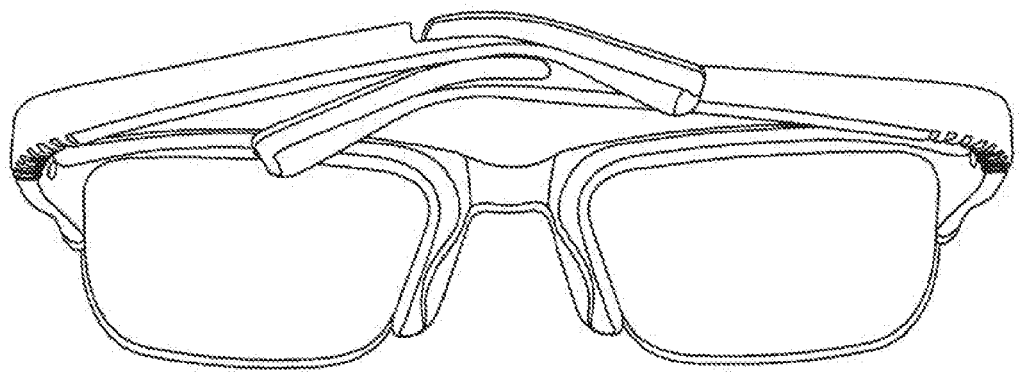
Figure 11C:
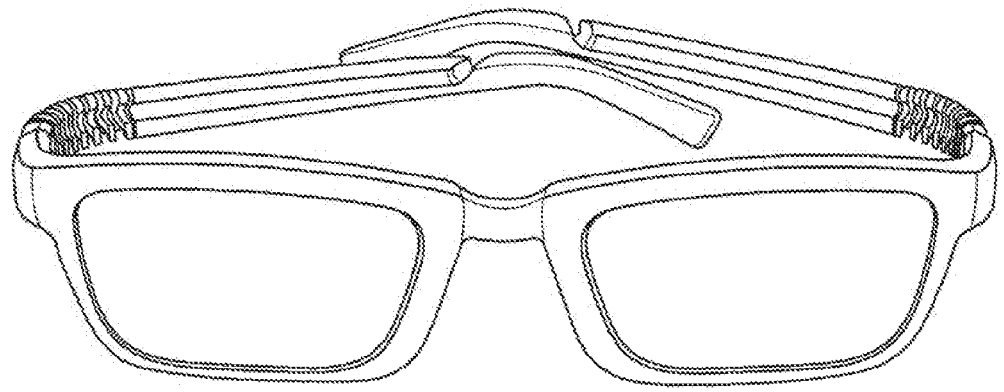
Figure 11D:
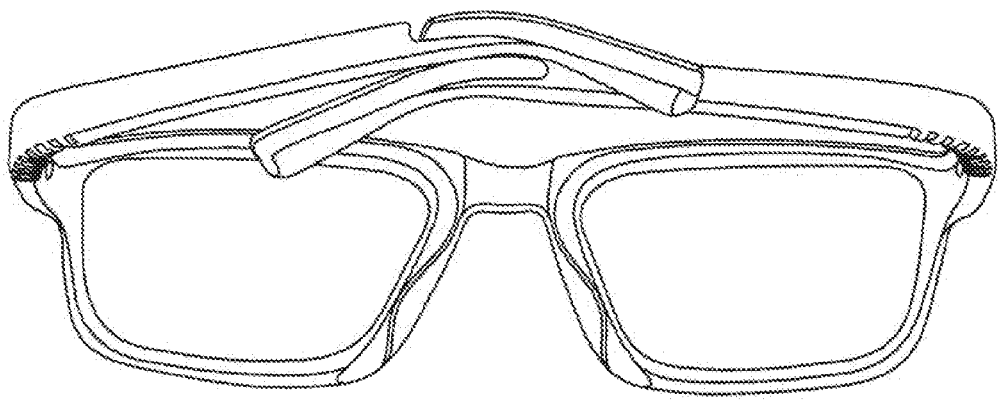
Figure 12A:
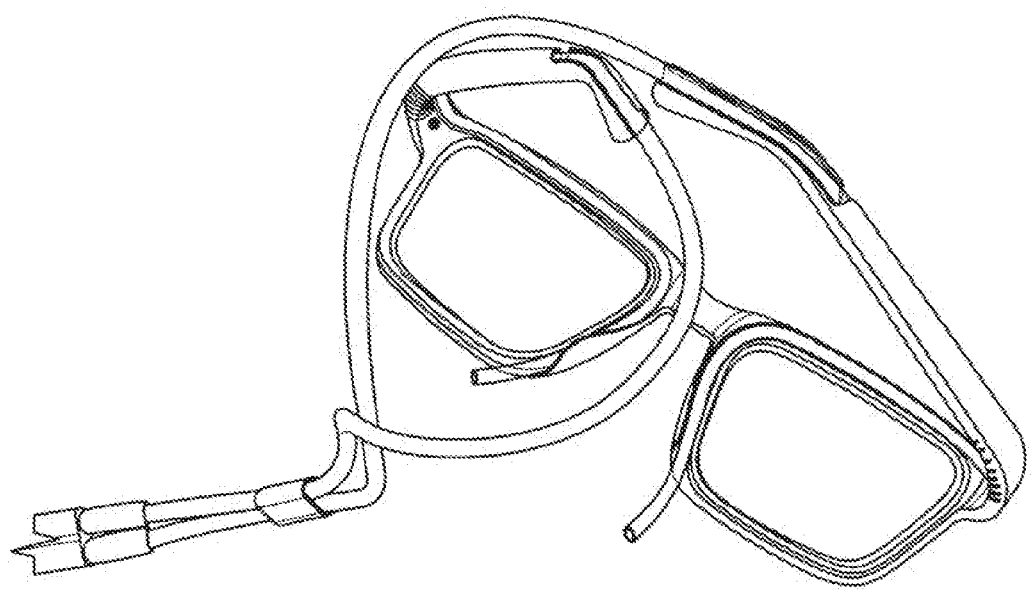
FIG. 12A shows the back view of the eyeglasses frame.
Figure 12B:
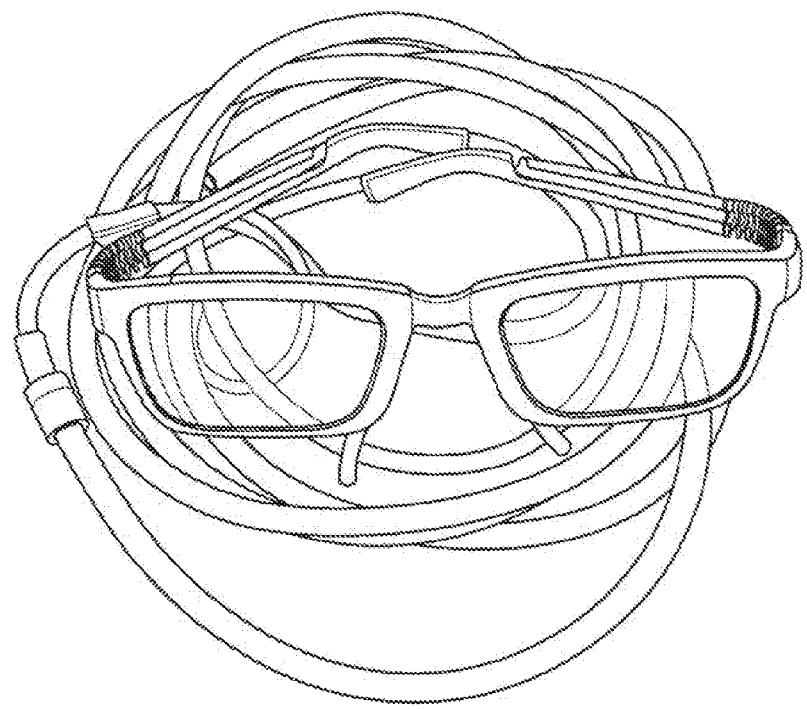
FIG. 12B shows the front view of the eyeglasses frame which would be visible to an observer facing the wearer of the frame.

As can be seen in FIG. 8, the oxygen administration means also comprise two tube parts (91,91'), which extend, during use, into the two nostrils of the user. The tube parts (91,91') are in this case formed by folded end parts (64,64') of the hoses (6,6'). FIGS. 9 and 10, finally, show a device (10) according to the invention with the eyeglasses (1) clamped therein. The device (1) comprises a third means for mutually correct positioning of the tube parts (91,91') casu quo the bent end parts (64,64') and the eyeglasses (1), here in the form of an interchangeable part (11) that can be tailor-made and thus adjusted to an individual user.

The invention makes it possible for the hoses from the oxygen administration means to be as far removed from sight as possible. In addition, readily-available standard tubes are used which can always easily be replaced. The hoses can be easily fitted in the eyeglasses, thus placing the assembly of eyeglasses and oxygen administration means is simple for a user.

It should be clear that the invention is not limited to the embodiments given, but that within the scope of the invention all sorts of obvious variations would be possible to a skilled person. The invention advantageously may also be employed in the administration of a gas other than oxygen.

Another aspect of the present disclosure relates to eyeglasses (1) comprising a structure (3) suitable for holding lenses (4,4') and temples (5,5'), characterized in that the temples are provided with a receiving space (51,51') suitable for receiving a part (61,61') of a hose (6,6') and a hinge (7,7') between the frame and temple, characterized in that the eyeglasses are provided with a first means suitable for guiding of a part {63, 63'} of a hose (6,6') in the vicinity of the hinge so as to guarantee a desired minimum bend radius of the part of the hose.

A further aspect of the present disclosure relates to eyeglasses (1) comprising a structure (3) suitable for holding lenses (4,4') and temples (5,5'), characterized in that a temple is provided with a receiving space (51,51') suitable for receiving a part (61,61') of a hose (6,6') and a hinge (7,7') between the frame and temple, characterized in that the eyeglasses are provided with a first means suitable for guiding of a part {63,63'} of a hose (6,6') in the vicinity of the hinge such that the part of the hose is not shortened or extended when the temple and the frame are mutually hinged.

In some embodiments, the eyeglasses are characterized in that the eyeglasses are provided with a first means suitable for guiding of a part {63,63'} of a hose (6,6') in the vicinity of the hinge so as to guarantee a desired minimum bend radius of the part of the hose and such that the part of the hose is not shortened or extended when the temple and the frame are mutually hinged.

The first means may comprise a plurality of repeating units which move relative to one another. The first means may comprise a plurality of hinged parts. In certain embodiments, the first means forms a part of the hinge. For example, the first means may be a structure distinct from the hinge, or the first means may be at least a part of the hinge, or the first means and the hinge may be the same structure.

In some embodiments, the first means forms a part of the hinge comprising a plurality of ribs each connected to a segment of a spine. The plurality of ribs may contact a central spine, in a similar manner to the ribs which contact the spinal vertebrae in a human. The spine may comprise segments like vertebrae, or the spine may be one continuous piece. In either case, each of the ribs (or each of the pairs of ribs facing each other) may hinge independently of the other ribs (or pairs of ribs).

In some embodiments, the first means is a flexible element such as a hinge. Exemplary embodiments of flexible elements are shown in FIGS. 16-21. The flexible elements may comprise a plurality of repeating units which are operatively connected to one another, either by linking separate units as in FIGS. 16 and 17, or because the flexible element is constructed from one integral piece of material.

Exemplary Eyewear—Eyeglasses with Grooves and Flexible Elements (Hinges)

Another aspect of the present disclosure relates to eyewear comprising a flexible element such as a hinge. Eyewear may include any of a variety of devices for aiding vision or protecting the eyes, such as goggles, eyeglasses (also called spectacles, specs, glasses, blinkers), or a variation of eyeglasses such as a lorgnette, monocle, or pince-nez, or sunglasses (also called shades). The eyewear may be an eye mask or eye patch. The eyewear may have at least one corrective lens that is a single focus lens, a bifocal lens, a trifocal lens, or a multi-focal lens, and/or may have at least one of a tint, color, finish, or filter, such as polarization. Eyewear may also be non-optical or non-corrective, for example, eyewear having lenses that do not alter visual performance as compared to the user's eye in the absence of the eyewear.

In some embodiments, the eyewear is eyeglasses. Typical parts of eyeglasses may include temple tips (also called ear pieces, which are the end of the temples and the part of the eyeglasses which contact the user's ears and/or the user's head near the ears); temples (also called temple pieces, legs or sides); hinges or flexible elements that bend so the temple pieces move in relation to the rims; rims (also called eyewires, particularly when the rims are constructed from thin metal or wire), which may refer to upper rims, lower rims, both the upper and lower rims collectively, or to a partial rim which surround the lenses; a bridge which connects the two rims (or in the case of rim-less glasses, the bridge may directly connect the two lenses); a frame front (the front part of the eyeglasses such as the rims and bridge, not including the temples); end-pieces (a part of the frame which extends from the lenses and 16 contacts the temples, for example, to connect the hinge to the frame front); and nose pads which are the part of the eyeglasses that contact on the nose. Some models also include parts like a top bar, a double bridge, removable nose pads which are connected to the frame front by nose pad arms, and/or screws which attach various parts of the eyeglasses to each other, such as the temples attached to the end-pieces or the temples attached to the frame front.

In certain embodiments, the eyewear is configured for receiving a hose. The hose may be a hose suitable for medical gas therapy, such as a hose for oxygen therapy. The hose may be a hose suitable for controlled oxygen therapy, helium therapy, carbon dioxide therapy, nitrogen therapy, hyperbaric oxygenation, or inhalational anesthetics. The eyewear may be configured for receiving a hose that is part of a chronic medical gas therapy administration apparatus.

The eyewear should enable free flow of gas through a hose that is fitted into the receiving space. For example, at least 50% of the gas from the gas source reaches the user. At least 60%, 65%, 70%, 75%, 80%, 85%, 90%, 95%, or 99% of the gas may reach the user. In some embodiments, at least 95% of the gas reaches the user.

Accordingly, a further aspect of the present disclosure relates to eyewear configured for receiving a hose, comprising: a first rim and a second rim; a first temple piece operatively coupled to the first rim; a second temple piece operatively coupled to the second rim; wherein the first temple piece and the second temple piece are operatively coupled to the first rim and the second rim, respectively, by first and second flexible elements each having a spine and a plurality of ribs, and wherein the eyewear comprises a first groove defined in and extending through the first rim, the plurality of ribs of the first flexible element, and the first temple piece, wherein the groove is defined in an inner surface of the first temple piece adjacent the first flexible hinge, wherein the first groove transitions to an outer surface of the first temple piece distally from the first flexible element, and wherein the eyewear includes a second groove defined in and extending through the second rim, the plurality of ribs of the second flexible element, and the second temple piece, wherein the groove is defined in an inner surface of the second temple piece adjacent the second flexible hinge, wherein the second groove transitions to an outer surface of the second temple piece distally from the second flexible hinge. In some embodiments, the first and second grooves are channels, for example, open channels. They may be open on one side, for example, on an open side that is facing towards the user's face during use of the eyeglasses. The channels may also be closed channels, such as a hollow that is open at both ends but sealed along its length. The channel may be an open channel that has a door, seal, flap to close the open channel, or a cover that attaches to the open side of the channel in order to close it. A groove (also called receiving space, gutter, track, moat, canal, holder, guide, furrow, hollow, notch, canyon, or valley) may take the form of a channel that is either open or closed.

One aspect of the present disclosure relates to eyeglasses configured for receiving a hose, such as a hose delivering oxygen for oxygen therapy. Features of the eyeglasses: a flexible hinge which will bend so glasses can be folded, but will not allow the hose to kink, pinch, or close off the flow of oxygen through the hose; the flexible hinge may have a spine portion and ribs; and a groove configured to receive the hose. The groove runs along the length of the temples, at least the upper rim of the frame (also possible that there could be a groove in the lower rim of the frame), and the nosepad area. The groove may be open on one side (so that the hose may be pressed into place), or may be a fully-closed channel (so that the hose is fed through the channel). In the temple, a first portion of the groove runs along the inner surface of the temple while a second portion of the groove runs along the outer surface. This secures the hose, preventing it from sliding longitudinally along the groove and out of the eyeglasses.

In some embodiments, the eyewear comprises a flexible element, wherein the flexible element is a structure comprising mutually hinging parts and/or interlocking mechanisms. The parts may fit together like a jigsaw puzzle, but bend around a hinge axis at the intersection of the parts. FIG. 16 shows an exemplary embodiment. Here, the flexible element comprises a plurality of parts which connect to one another through a connecting means which may include but are not limited to a screw, clip, peg and hole. Each part hinges a round a hinge axis created by the intersection of the part with its neighboring part. Together, the parts make up a flexible element that, in eyewear, bends as the temple pieces of the eyeglasses are closed, but not do bend far enough to pull, kink, twist, bend, or fold the hose. FIG. 17 shows another exemplary embodiment, in which the plurality of pieces have corners with a thicker, boxier shape than the embodiment in FIG. 16.

In certain embodiments, the flexible elements have limited flexibility in all directions, so there is limited bending or folding of the temple pieces. For example, if the flexible elements bend less than 45° (for example, the flexible elements bend about 0°, 15°, 30°, 45°), then the temple pieces may not be folded or bent enough to move them towards the frame front. Similarly, if there is no flexible element between the temples and frame front, and the temple pieces do not move relative to the frame front. Accordingly, a hose that has been placed in this eyewear will never reach its minimum bend radius.

In certain embodiments, the temple pieces are detachable from the frame front, and may be folded or bent in relation to the frame front when a hose is fitted into the eyewear. The hose functions as the flexible element.

A. Eyewear Rims

In eyewear models having one or more rims, each rim surrounds a lens, either partially or fully. In some eyewear models, a rim and nose pad are one continuous piece wherein the nose pad extends from the rim. In contrast, other eyewear models feature a nose pad that is a separate piece from the rim, and is typically attached to the rim via a nose pad arm. The models with separate nose pads are often wire rimmed eyeglasses, or rim-less eyeglasses, although it is also possible to attach separate nose pads to any model of eyeglasses, even models which already have a continuous nose pad extending from the rim.

In some embodiments of the eyewear disclosed herein, the eyewear comprises at least one rim having a nose pad attached thereto in a continuous piece. Both rims may have nose pads attached. This eyewear comprises a groove defined in the nose pad, for example, in the inner surface of the nose pad. The groove is configured for receiving a hose.

In certain embodiments, the eyewear comprises a groove configured for receiving a hose, but the groove does not extend along the nose pad. For those eyewear models in which the nose pad is a separate piece attached to the rim rather than being continuous with the rim, it may be challenging to place a groove configured to guide the hose along the nose pad arm and the nose pad. Accordingly, the eyewear may have an opening in the rim configured so that a hose can extend directly from the rim to reach the side of the nose of the patient. The eyewear may also comprise an additional piece attached to the rim, which additional piece is configured to guide the hose from the groove in the hose along the side of the patient's nose. The additional piece may be attached to the rim as an integral, continuous, single piece, or may be a separate piece that is attached to the rim. The additional piece may be a small channel, either open or closed, or a may be a substantially flat like a nose pad.

In some embodiments, at least one of the first and second rims is a full rim which surrounds the lens. For example, the rim may be continuous around the edge of the lens so that it completely and wholly surrounds the lens. The rim may be substantially continuous around the edge of the lens so that it surrounds the majority of the lens, but not the entire lens. Such a rim may surround more than 50% of the lens. In certain embodiments, at least one of the first and second rims is a half rim which surrounds about half (50%) of the lens it holds. At least one of the first and second rims may surround less than 50% of the lens.

The first and second rims, whether a full-rim or a half-rim style, may guide and conceal a part of the hose. The first and second rims have a first and a second groove, respectively, defined in and extending through them. In some embodiments, the first and second groove are each configured to receive a hose. The grooves may be located on the inner surface of the first and second rims, so that the grooves and any hoses fitted into the grooves are hidden from view. The grooves may be open channels where the open side of the channel is facing the user's face during use of the eyewear.

In some embodiments, the first and second rims of the eyewear surround more than 50% of the lenses, and surround both the upper edge of the lens and the lower edge of the lens. Each of the first and second rims have a groove configured to receive a hose, for example, on the inner surface of the rims, and further, the groove in each of the rims extends both along the upper edge of the rim and the lower edge of the rim. In this eyewear, a hose can be split, so that a first half of the hose extends along the groove in the upper edge of the rim and a second half of the hose extends along the groove in the lower edge of the rim. The split hose then rejoins to form a single hose near the nose pad or a part of the rim where the hose exits the rim. In this way, the parts of the hose which extend along the rims need only be half the diameter of the part of the hose that is not split. In such a configuration, thinner hoses can be used without compromising the overall capacity of the hose. This provides flexibility to use eyewear rims of different thicknesses, for example, rims which are thinner than the diameter of the whole hose, but still thicker than the diameter of the split hose. Such rims will still conceal two halves of the split hose.

The first and second rims may be fixedly joined together by a bridge, for example, a bridge that is constructed as a single monolithic piece with the first and second rims or attached by fastening means such as a locking clip or pin mechanism; by an adhesive such as a long-lasting adhesive; or by a joining process such as welding, sintering, fusing which joins the rims to the bridge. In certain embodiments, the first and second rims are not fixedly joined to the bridge. For cleaning or storage of the eyewear, it may be advantageous to separate the eyewear into two halves. The first and second rims could be attached to the bridge by screws, fasteners, locks, adhesives, magnets, interlocking parts, or through intermediate parts which can be loosened or removed to separate the rims from the bridge. The bridge may also be formed from two half bridges which are held together during use of the eyewear but separated into the two halves when the eyewear is not used. Separable eyewear may also be advantageous when one half of the eyewear is broken or damaged and is easily exchanged for a new half. Separable eyewear may be used if a frame is asymmetric, for example, because of asymmetry in the user's eyes, face, ears, or parts of the head.

B. Eyewear Temple Pieces

In certain embodiments, the eyewear comprises a first temple piece operatively coupled to the first rim and a second temple piece operatively coupled to the second rim by first and second flexible elements, such as hinges. Any of these parts (rim, flexible element, temple piece) may be constructed as a plurality of separate pieces which are then operatively coupled to form the eyewear, or parts may be integrally formed with one another into single monolithic pieces. Parts may be combined, such that two or more parts form one single monolithic piece which is operatively coupled to a single part, or operatively coupled to another monolithic piece formed from two or more parts.

For example, a rim, flexible element, and temple may all be separate parts that must be joined together. Alternatively, these parts may integrally form a single monolithic piece of eyewear comprising a first rim, a first flexible element, a first temple, a second rim, a second flexible element, and a second temple. The eyewear may further comprise a bridge that is part of the single monolithic piece of eyewear, or, alternatively, may comprise a separate bridge (or two half-bridges) that are operatively coupled to the rest of the eyewear.

The first temple piece may be integrally formed as a single monolithic piece with the first flexible element and/or the second temple piece may be integrally formed as a single monolithic piece with the second flexible element. In a single monolithic piece, the temple piece and the flexible element form a one-piece, solid, or unbroken construct. Thus, the parts may be operatively coupled via a solid, unbroken construct.

The first temple piece may be separate from the first flexible element and/or second temple piece may be separate from the second flexible element. In this case, the parts may be operatively coupled with screws, fasteners, locks, adhesives, magnets, interlocking parts, or through intermediate parts that couple with the temple piece on one side and the flexible element on the other side.

In some embodiments, the first flexible element is integrally formed as a single monolithic piece with the first rim and/or the second flexible element is integrally formed as a single monolithic piece with the second rim. Accordingly, the first and second temple pieces may each be separate pieces that are integrally formed with the single monolithic piece formed by the flexible element and the rim. The first and second temple pieces may be operatively to the first and second flexible elements, respectively, with coupled with screws, fasteners, locks, adhesives, magnets, interlocking parts, or through intermediate parts that couple with the temple piece on one side and the flexible hinge on the other.

It certain embodiments, the first temple piece comprises a first flexible element and/or the second temple piece comprises a second flexible element. These flexible elements may be integrated into their respective temple pieces, so that effectively the temple piece is a flexible temple piece, for example, a hinged temple piece. The flexible element need not be considered as a separate structure in those embodiments where the temple piece comprises an integrated hinge structure.

C. Groove

In some embodiments, the eyewear is configured for receiving a hose and comprises a groove configured for receiving a hose. A groove (also called receiving space, gutter, track, moat, canal, holder, guide, furrow, hollow, notch, canyon, or valley) may take the form of a channel that is either open or closed. The groove may have dimensions which correspond to a specific hose that will be used with the eyewear.

The groove may be fully closed, like a closed channel, wherein the diameter of the hollow within the closed channel is equal to or slightly larger than the diameter of the hose so that the hose fits into the channel.

The groove may be an open channel, wherein the cross section of the open channel is a semi-circle having a diameter that is equal to or slightly larger than the diameter of the hose. The cross section of the open channel may be any polyhedral shape or a part of the shape (such as a partial square), as long as the open channel is large enough to accommodate the hose. The opening of the channel should typically be the same diameter or a smaller diameter than the diameter of the hose, in order to ensure that the hose will be held securely in place. The secure hold may result from pressure exerted on the hose from the walls of the open channel, from the edges at the opening, and/or from protrusions or other geometric features on the inside of the channel which lock the hose into place. Because of the open side, the hose can be easily pressed into the open channel, so that the hose is securely fitted (e.g., clamped or clicked into place and fittingly held) in the open channel. The edges of the open channel may be angled, curved, beveled, tapered or otherwise shaped into a form configured to hose securely in place. Nonetheless, the groove (or open channel) may not be configured to hold the hose so tightly that the groove damages the hose or blocks oxygen flow. In addition, the groove may be configured so the hose can be readily removed and replaced with a new hose.

Each of the parts of the eyewear may comprise a groove defined in and extending through the parts. The eyewear may comprise a first groove defined and extending in first parts (for example, a first rim, a first flexible element, and a first temple piece) and a second groove defined in and extending in second parts (for example, a second rim, a second flexible element, and a second temple piece). In some embodiments, first and second nose pads may also have a first and second groove defined in and extending through them. A nose pad having a groove may be attached to the rim, for example as a continuous piece.

The groove may extend centrally along the longitudinal axis of each part of the eyewear, so that a hose positioned in the groove is approximately in the center of the structure (e.g., the center of the temple piece or the flexible element), relative to the walls of its inner and outer surface. Notably, if a hose were positioned on the outer wall of the flexible element, for example, if the hose were not positioned within a central groove, then the bending of the flexible hinge could cause the hose to stretch or lengthen. Conversely, if a hose were positioned directly on the inner wall of the flexible element, for example, if the hose were not positioned within a central groove, then the bending of the flexible hinge could cause the hose to shorten or compress. In either case, the hose could be weakened, damaged, or torn, especially after repeated bending of the flexible element in the eyewear. Accordingly, a groove that positions the hose in a central location in the eyewear helps to prevent mechanical damage to the hose.

The groove may follow a continuous (e.g., uninterrupted) path throughout the eyewear so that the complete eyewear, which is assembled if parts are separate or which is one-piece if the eyewear is a single monolithic piece, has a continuous groove extending through the temple to the hinges (or the vicinity of the hinges) to the rims. The groove may extend to through the nose pads if the eyewear has nosepads that are attached the rim, for example as a continuous piece. This groove is configured for receiving a hose that will extend from the distal ends of the temple to the rims (and optionally to the nose pads). The hose will exit the eyewear and terminate in tube parts that curve around the side of the user's nose and extend at least partially into the nostrils of the user. The tube parts may be separate from the hose and attached to the hose ends, for example, if the tube parts are one-piece nasal prongs available for use with other oxygen delivery systems. The tube parts may be individual nasal prongs, for example, a first curved tube piece that channels oxygen to the first nostril and a second curved tube piece that channels oxygen to the second nostril. Or, the tube parts may be the ends of the hose which have been bent and converted into a curved shape that is suitable for extending at least partially into the nostrils of the user.

It is desirable to conceal a hose from view. Accordingly, in some embodiments, the groove is a closed channel and the hose is positioned inside the channel. In certain embodiments, the groove is an open channel and is defined in an inner surface of each of the temple, hinge, and rim if the eyewear has a nose pad that is attached to the rim, for example as a continuous piece, then the open channel is also defined in an inner surface of the nose pad. This groove is facing towards the user's face when the eyewear is in use. This ensures that a hose placed into the groove is hidden from view, giving an outward effect similar to the closed channel. The hose is more easily placed into an open channel than a closed channel, as the hose can be pressed into the open channel from its open side, rather than threading it through the length of the closed channel.

In certain embodiments, the groove is defined on an inner surface of the temple piece adjacent to the hinge, and the groove transition to an outer surface of the temple piece distally from the flexible hinge. A hose placed into this groove would be hidden from view for most of the length of the eyewear, and would only be visible at a distal part of the temple piece. The distal part could be at the temple tips, for example, at the part of the temple piece that is near to the ears of the user. The groove may transition to the outer surface at such a position that the hose placed into the groove is hidden partially or fully behind the ears of the user.

A groove that transitions from the inner surface to the outer surface of the temple piece is suitable for positioning a hose securely in the groove and minimizing or eliminating sliding, shortening, or extending of the hose when the eyewear used. Hoses can slide longitudinally out of channels or grooves in eyewear, for example when the temple pieces are opened and closed, but a hose placed into a groove that transitions from an inner surface to an outer surface of the temple piece may have an extra curve at the transition point that provides stability and minimizes longitudinal movement. As described above, the groove is centrally located, which also helps to minimize stretching and compression of the hose at the flexible elements.

Another advantage of the transitioning groove is that contact points of the hose and the user's face and/or ears are minimized. The temple tips contact the user's face and ears, and it may cause discomfort in some situations if a hose is also fitted into the inner surface of the temple tips at these contact points. For example, a hose on the inner surface may press against the head and ears of the user, or may become entangled in the user's hair. In addition, dirt or oil from the user's head and ears may collect in and around the hose. Accordingly, if the groove is configured so that a hose is guided away from the inner surface at the distal parts of the temple (including the temple tips), then the eyeglasses may be more comfortable for the user and easier to keep clean. Much of the hose is still discreetly concealed, as it is placed into a groove on the inner surface of the eyeglasses. The relatively small parts of the hose that are visible in the grooves on the outer surface of the temples may be concealed by the ears or the hair of the user.

D. Flexible Element

A further aspect of the present disclosure relates to a flexible element such as a hinge for use in eyewear. In some embodiments, a flexible element is a hinge. A flexible element may be a structure positioned between a temple piece and a frame front, which enables the temple piece to move, fold, or bend in relation to the frame front. A flexible element may be integrated into the frame front, rim, and/or integrated into the temple piece, or the flexible element may be a separate piece of the eyewear that is assembled with the other parts to make a complete eyewear product. In some embodiments, a flexible element integrated into a rim produces a flexible rim or a flexible element integrated into a temple piece produces a flexible temple piece. Accordingly, a flexible element need not be a distinctive structure apart from the rim and/or the temple piece. Where the flexible element is a hinge, the hinge need not be a distinctive structure apart from the rim and/or temple piece. Indeed, eyewear models have been described in the art as "hingeless" because they do not have a standard or traditional eyeglasses hinge mechanism, such as a barrel hinge or spring hinge, where screws are used. Exemplary hingeless eyeglasses are typically eyeglasses in which a flexible strip of titanium or a bendable structure is positioned between the temple pieces and the rims, or, for those eyeglasses that do not have rims, positioned between the temple pieces and the lenses. Thus, a flexible element such as a hinge is any flexible structure positioned between a frame front and a temple piece which enables or mediates movement of the temple piece in relation to the frame front, even if the flexible element is integrated into the temple piece or the frame front and even if the resulting eyewear could be described as "hingeless" because it does not include a standard or traditional eyeglasses hinge mechanism.

In some embodiments, the flexible element is a structure comprising mutually hinging parts and/or interlocking mechanisms. The parts may fit together like a jigsaw puzzle, but bend around a hinge axis at the intersection of the parts. FIG. 16 shows an exemplary embodiment. Here, the flexible element comprises a plurality of parts which connect to one another through a connecting means which may include but are not limited to a screw, clip, peg and hole. Each part hinges around a hinge axis created by the intersection of the part with its neighboring part. Together, the parts make up a flexible element that, in eyewear, bends as the temple pieces of the eyeglasses are closed, but not do bend far enough to pull, kink, twist, bend, or fold the hose. FIG. 17 shows another exemplary embodiment, in which the plurality of pieces have corners with a thicker, boxier shape than the embodiment in FIG. 16.

Figure 6:
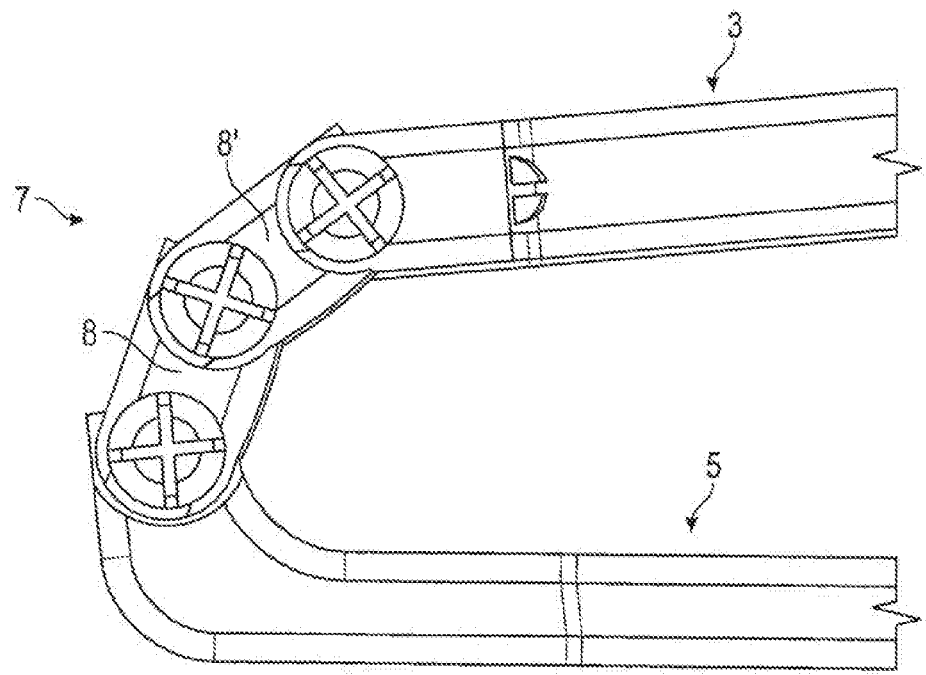
FIG. 6 is a top plan view of a detail of the eyeglasses.
Figure 7:
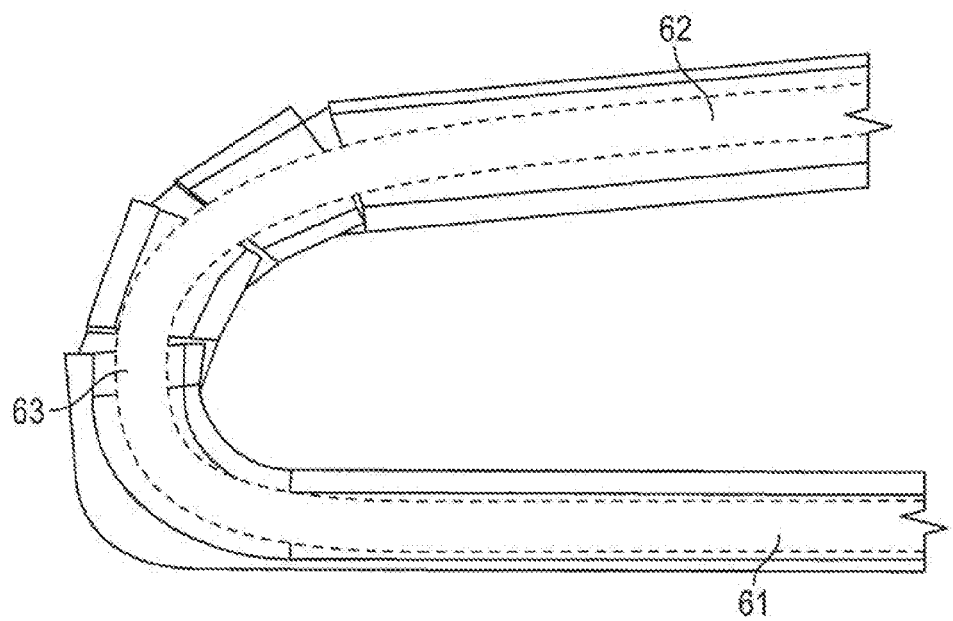
FIG. 7 is a sectional view thereof with a part of a hose (dashed line)

In some embodiments, the flexible element comprises a plurality of repeating units, which are operatively connected to one another, either by linking separate units as in FIGS. 16 and 17, or because the flexible element is constructed from one integral piece of material (see exemplary embodiments in FIGS. 18-21). The repeating units may be operatively connected to one another via screws, clips, snaps, or other connecting means. An exemplary connection is shown in FIG. 6, an example of a flat snap mechanism that joins two parts and is secured by pressing on each of the 4 quadrants of the snap. Connecting means may create a hinge axis around which the repeating units move.

The repeating units may be positioned so that they are visible on the outer surface of the eyewear, or they may be positioned so they are facing the user's face and are partially visible or not visible.

In certain embodiments, the flexible element comprises a spine. For example, the flexible element may be a hinge or a flexible hinge comprising a spine. An exemplary spine is a rectangular structure having a length that is longer than its width and a thickness (height) that is shorter than its width. Other exemplary spines are elongated structures such as curved lines, coils, springs, intertwined wires, lattice structures, or shapes like cylinders or columns which have polyhedral shaped cross sections and which may be hollow or solid. Spines may comprise individual units which are operatively coupled, such as mutually hinging parts. The mutually hinging parts such as those found in a cable carrier may form the individual units of a spine. Individual units may also be stacked in a column, with compressible materials interspersed between the individual units. An exemplary spine comprises individual units stacked like human vertebrae, where a hose runs through the length of the spine in manner like a spinal cord, for example, being pressed into an open channel on one side of the spine. The open channel of the spine should be facing towards the user's face during use of the eyewear.

The flexible element may be a hinge comprise a spine and a plurality of ribs. Ribs may project from only one side of the spine, or may project from more than one side of the spine. For example, ribs may project radially from the spine a long its length. The ribs projecting radially from one side of the spine may project in the same direction originating from a straight line along the spine. In addition, ribs may project in pairs, so that each rib which projects radially from the spine along a side of spine's length has a corresponding rib projecting radially from the spine along the opposite side of the spine's length. In some embodiments, the ribs are curved. Each pair of curved ribs, together with the spine, may form segments of a C-shaped channel into which a hose can be fitted. In some embodiments, the ribs are joined to form a closed channel. In certain embodiments, the ribs are not joined, but leave an open channel into which a hose can be fitted. The open side of the channel should be facing the user's face, so that the hose that is fitted into the channel is less visible. In some embodiments, the edges of the ribs are angled, curved, beveled, tapered or otherwise shaped into a form configured to hose securely in place. It is possible that the ribs projecting along a first side of the spine's length are less curved than the ribs projecting along the opposite side of the spine's length. Similarly, the length of the ribs projecting along a first side of the spine's length may be shorter than the length of the ribs projecting along the opposite side of the spine's length. The length of the ribs and/or the curve of the ribs may correspond to the size of hose that the ribs will accommodate.

The ribs may be curved. The curve may correspond to the outer surface of a hose, so that the curved ribs hold the hose in place. The curve may have a radius that is substantially equal to the radius of the open channel in the eyeglasses. In some embodiments, the open channel is defined in an inner surface of the temples adjacent to the flexible element, wherein the open channel transitions to an outer surface of the temples distally from the flexible element.

A flexible element may bend more readily in a first direction than in a second direction, for example, because two or more parts in the flexible element contact one another and prevent further movement. For example, the hinge comprising a spine and a plurality of ribs may bend more readily in a first direction than in a second direction, for example, because the ribs may contact each other when the hinge is bent in the second direction. In such an example, the length of the ribs affects the extent to which the hinge bends. In certain embodiments, when the eyeglasses are used with the hose of an oxygen administration means, the eyeglasses must not pinch, kink, or damage the hose, or otherwise block the flow of oxygen through the hose. Accordingly, the length of the ribs in the hinge may be set so they will contact each other at such a point that the hinge does not bend further, and thus a hose positioned in the vicinity of the hinge will also be limited in its bending. This protects the hose from pinching, becoming pulled, kinked, or other damage, and prevents disruption in the flow of oxygen. Thus, a hinge with ribs which contact one another and prevent further bending of the hinge and hose may guide of a part {63,63'} of a hose (6,6') in the vicinity of the hinge so as to guarantee a desired minimum bend radius of the part of the hose. The limited bending conferred by the contact of the ribs with one another guarantees the minimum bend radius of the part of the hose is guaranteed. In certain embodiments, a hinge with ribs guide a part {63,63'} of a hose (6,6') in the vicinity of the hinge in such a way that the part of the hose is not shortened or extended when the temple and the frame are mutually hinged.

A number of parameter affect the bending of a flexible element such as a hinge. The dimensions of the flexible element (length, height, wall thickness) affect the ability of the flexible element to bend. For those flexible elements comprising a plurality of units, the number of units, spacing between the units, orientation of units, type of connection between units, shape of the units, and dimensions (length, height, width) of the units affect the ability of the flexible element to bend. For example, where a flexible element is a hinge having a spine and a plurality of ribs, the length of the spine, the height of the spine, the wall thickness all affect the stiffness, strength, and flexibility of the hinge, as do the number of ribs, amount of space between the ribs, orientation of the ribs, and length of the ribs. In general, a thinner wall will be more flexible but less stable than a thicker wall. If the wall of the spine is too thin, then they will not hold the frame in a stable position relative to the user's face, and the temples may separate too far from each other, so that they cannot secure the eyewear against the side of the user's head. Conversely, a thicker wall will be less flexible than a thinner wall. A thick wall that is inflexible may break when bending.

The material used to construct the flexible element affects the bending of the flexible element. Some materials are more flexible than others. Exemplary materials for flexible elements and all parts of eyewear include but are not limited to metals (such as titanium, aluminum, or stainless steel), metal alloys, memory materials, copper beryllium, carbon fiber, cellulose acetate, cellulose propionate, nylon, bone, mixtures of metal and polymers such as alumide, polyamides (PA) such as PA10 and PA12, and thermoplastic urethanes (TPU). A material such as TPU is more flexible than PA12, so a flexible element made from TPU would be more flexible than one made of PA12.

An exemplary flexible element made of PA12 and having a length between 15-25 mm, a height between 6-10 mm and a wall thickness around 1 mm (between 0.5-2.0 mm) would be expected to bend into a curve with a radius of about 10-12 mm.

Accordingly, a spine with a thick wall may guide of a part {63,63'} of a hose (6,6') in the vicinity of the hinge so as to guarantee a desired minimum bend radius of the part of the hose. The limited bending conferred by the thick wall of the spine guarantees the minimum bend radius of the part of the hose is guaranteed. In certain embodiments, a hinge with a thick wall guides a part {63,63'} of a hose (6,6') in the vicinity of the hinge in such a way that the part of the hose is not shortened or extended when the temple and the frame are mutually hinged.

In some embodiments, the dimensions of the flexible element, the features of repeating units, if any, as well as the materials of the flexible element, are selected on the basis of their bending capacity, and the flexible element for the eyeglasses described herein is designed on the basis of desired bending. For example, if the minimum bend radius of a hose (for example, the minimum bend radius is typically 3× the diameter of the hose), then the material for the flexible element, dimensions, and other factors can all be optimized to guarantee the minimum bend radius of the hose.

A further aspect of the present disclosure relates to a flexible hinge for eyewear. Features of the hinge: spine (backbone) and ribs. Ribs may be C-shaped; degree of bending may be limited by the thickness of the spine and/or wall of the spine. Degree of bending may also be limited by the size of the ribs, for example, further bending may be prevented when the ribs contact each other. Hinge may be integrated into a temple, rim, and/or frame, or may be a separate piece that can be attached. Hinge may have a groove configured for receiving a hose.

Assembly and Tools

Another aspect of the present disclosure relates to an assembly (or construction) of eyewear and an oxygen administration means, such as a hose. A further aspect of the present disclosure relates to a device (10) for fitting the hose in the eyewear such as eyeglasses disclosed herein. In some embodiments, the device is complementary in shape to the eyewear or to the frame of the eyewear, so that the eyewear fits into the device. As shown in FIG. 9, the device has protruding parts (12) which are suitable for suitable for support on a surface such as a table or countertop. The eyeglasses can be placed into the device, with the supports contacting the surface. The eyeglasses would not contact the surface, and would be protected from damage. In particular, the lenses may be susceptible to scratching or scraping if the hose were pressed into the open channel of the eyeglasses while resting the eyeglasses directly on a surface. The device as disclosed herein may be custom fitted to the eyeglasses of an individual user, and may accordingly be tailor-made and adjusted to an individual user. In certain embodiments, the device may be a general device configured to fit a variety of different sizes of eyeglasses, or may be a combination of parts that are general for any eyeglasses and parts that are custom-sized for an individual user. Another aspect of the present disclosure relates to a device (10) comprising means suitable for positioning the hose (e.g., the bent ends of the hose), for example, mutual positioning of the end parts of the hose relative to the eyewear.

Eyewear Manufactured by Additive Manufacturing (AM)

Another aspect of the present disclosure relates to a method for manufacturing eyewear configured for receiving a hose, where in the method comprises obtaining a digital file representing an eyewear design and building the eyewear by an additive manufacturing (AM) process. In some embodiments, the eyewear configured for receiving a hose comprises a first rim and a second rim; a first temple piece operatively coupled to the first rim; a second temple piece operatively coupled to the second rim; wherein the first temple piece and the second temple piece are operatively coupled to the first rim and the second rim, respectively, by first and second flexible hinges having a spine and a plurality of ribs, and wherein the eyewear includes a first groove defined in and extending through, the first rim, the plurality of ribs of the first flexible hinge, and the first temple piece, wherein the groove is defined in an inner surface of the first temple piece adjacent the first flexible hinge, wherein the first groove transitions to an outer surface of the first temple piece distally from the first flexible hinge, and wherein the eyewear includes a second groove defined in and extending through, the second rim, the plurality of ribs of the second flexible hinge, and the second temple piece, wherein the groove is defined in an inner surface of the second temple piece adjacent the second flexible hinge, wherein the second groove transitions to an outer surface of the second temple piece distally from the second flexible hinge.

A digital file may be a CAD or CAM design, or may be a printable file. A printable file, for example in a format such as STL, comprises information about the shape and dimensions of the object as well as information about constraints which affect the ability of the object to be additively manufactured, such as the wall thickness of the parts of the object, the orientation at which the object should be manufactured, the complete surface of the object without any holes or missing parts (i.e., the eyewear is watertight), minimal thickness of cross-sectional layers that will form the object, angles and overhangs, support structures, and more. Thus, a printable file comprises values for these constraints which ensure that the object can be additively manufactured.

The printable file may be modified, for example, if the eyewear design is altered or the eyewear is custom fitted to a user's face. The printable file should remain printable even after modifications are made. In some embodiments, modifications made to the file correspond to changes in specific zones or regions of the eyewear (called "customization zones"), such as the bridge or the temple of the eyewear. These modifications, like lengthening the bridge width or shortening the temple length, are customizations that ensure that the eyewear better fits the anatomy of a user's face and head. Exemplary modification techniques comprise morphing, stretching, twisting, angling, bending, and radial scaling in the customization zones.

The eyewear may be fully customized or partially customized for an individual user. The eyewear may not be customized for an individual user, but is available in a range of standard sizes. Additive manufacturing processes may be used to manufacture of fully customized or partially customized eyewear, or standard sized eyewear that is not customized.

Additive manufacturing processes (also called 30 printing, rapid prototyping, additive fabrication, rapid manufacturing, freeform fabrication, layered manufacturing, rapid production or generative production) include but are not limited to stereolithography (SLA or SL), selective laser sintering (SLS or LS), selective laser melting (SLM or LM), selective deposition modeling (SDM), thermal stereolithography (TSL), fused deposition modeling (FDM), laser cladding, multi-phase jet solidification, ballistic particle manufacturing, particle deposition, optical fabrication, photo-solidification, solid imaging, resin printing, laser engineering net shape (LENS) fabrication as described in U.S. Pat. No. 6,459,951, scanning laser epitaxy (SLE) as described in W02014074947, selected area laser deposition (SALO) as described in U.S. Pat. No. 6,180,049. Any of these processes may be used to manufacture the eyewear described herein. The selection of a suitable AM process may depend, inter alia, on the materials used for printing and on the design of the object (i.e., eyewear) to be printed.

Uses and Users of Eyewear

The eyewear described herein has embodiments configured for receiving a hose, but the hose need not be present at all times. Eyewear with the features described herein may not have a hose. The eyewear may be worn with a hose at some times and without a hose at other times. In some embodiments, the eyewear is configured for receiving a structure that is fitted into the receiving space or groove like a hose although the structure does not function as a hose. For example, the structure may be a length of a polymer or metal that is fitted into the groove in order to provide additional shape, texture, structure, color, and/or decoration to the eyewear.

The eyewear may include optical lenses, such as corrective lenses. The eyewear may be used with lenses for correcting vision or for protecting the eyes, but it is also possible that the eyewear may be used solely as a holder for hoses or other structures, and would have dummy lenses.

A further aspect of the present disclosure relates to eyewear for use in delivering medical gas therapy such as oxygen therapy to users in need thereof. Some users require chronic gas therapy for as many hours in the day as possible. The users may be patients, for example, patients suffering from chronic pulmonary obstructive disorder (COPD), bronchitis, emphysema, lung cancer, pulmonary fibrosis, pneumonia, asthma, heart failure, cystic fibrosis, sleep apnea, cluster headaches, and other disorders which limit the ability of these patients to get adequate oxygen from the air. Thus, any patients requiring oxygen therapy, particularly long-term oxygen therapy, may use this eyewear. The eyewear may be worn at all times, also while the patient is sleeping.

The comfortable, discreet eyewear design is suited to users of chronic gas therapy, but it is also possible that other users may also be able to benefit from the advantages of the eyewear. Athletes who use oxygen for training or travelers who venture to high altitude locations may use the eyewear. Divers may benefit from eyewear such as googles having a groove or receiving space to receive an oxygen hose. In addition, those who work in air transport, such as airplane pilots and flight crews may use oxygen therapy. The eyewear may be substituted for other types of oxygen masks in some hospital or industrial settings, or may be used by emergency responders such as firefighters. Finally, other medical gases may be administered via the eyewear described herein, for example, inhalation anesthetics, helium therapy, carbon dioxide therapy, and nitrogen therapy.

The invention claimed is:

1. Eyewear configured for receiving a hose, comprising:
a first rim and a second rim;
a first temple piece operatively coupled to the first rim;
a second temple piece operatively coupled to the second rim;
wherein the first temple piece and the second temple piece are operatively coupled to the first rim and the second rim, respectively, by first and second flexible elements each having a spine and a plurality of ribs, and
wherein the eyewear comprises a first groove defined in and extending through the first rim, the plurality of ribs of the first flexible element, and the first temple piece, wherein the first groove is defined in an inner surface of the first temple piece adjacent the first flexible element, and
wherein the eyewear comprises a second groove defined in and extending through the second rim, the plurality of ribs of the second flexible element, and the second temple piece, wherein the second groove is defined in an inner surface of the second temple piece adjacent the second flexible element, wherein at least one of the plurality of ribs of the first flexible element or the plurality of ribs of the second flexible element is configured to form an open channel that is a part of at least one of the first groove or the second groove.

2. The eyewear of claim 1, wherein the first rim is attached to a first nose pad, and the second rim is attached to a second nose pad, and wherein at least one of the first groove or the second groove extends through the first and second nose pad.

3. The eyewear of claim 1, wherein the first and second flexible elements are each configured to hold a part of the hose in a curve larger than or equal to a minimum bend radius for the part of the hose.

4. The eyewear of claim 3, wherein the curve is larger than the minimum bend radius for the part of the hose.

5. The eyewear of claim 1, wherein the first and second flexible elements are each configured to hold a part of the hose in a fixed position that will not stretch or compress.

6. The eyewear of claim 1, wherein at least one of the first groove and the second groove is configured to hold a part of the hose in a fixed position that has no longitudinal movement when the first and second flexible elements are bent.

7. The eyewear of claim 1, wherein at least one of the first rim and the second rim is a full rim-style.

8. The eyewear of claim 1, wherein at least one of the first rim and the second rim is a half-rim style.

9. The eyewear of claim 1, wherein the first and the second rim are fixedly joined together by a bridge.

10. The eyewear of claim 1, wherein the open channel is configured to face a user's face when the eyewear is in use.

11. The eyewear of claim 1, wherein at least one of the first and second flexible elements is configured to move between at least two different positions comprising: a first position in which at least one of the plurality of ribs of the first flexible element or the plurality of ribs of the second flexible element do not contact each other; and a second position in which the at least one of the plurality of ribs of the first flexible element or the plurality of ribs of the second flexible element contact each other, thereby preventing the first and second flexible elements from bending further.

12. The eyewear of claim 1, wherein the first groove defined in the inner surface of the first temple piece and the second groove defined in the inner surface of the second temple piece are both configured to face towards a user's face when the eyewear is in use.

13. The eyewear of claim 1, wherein each of the first groove and the second groove transitions to an outer surface of the first and second temple pieces, respectively, at temple tips of the eyewear.

14. A method for manufacturing eyewear configured for receiving a hose, wherein the method comprises the steps of: obtaining a digital file representing an eyewear design of the eyewear according to claim 1, and building the eyewear by an additive manufacturing (AM) process.

15. Eyewear configured for receiving a hose, comprising:
a first rim and a second rim;
a first temple piece operatively coupled to the first rim;
a second temple piece operatively coupled to the second rim;
wherein the first temple piece and the second temple piece are operatively coupled to the first rim and the second rim, respectively, by first and second flexible elements, the first and second flexible elements each comprising at least one of a spine and a plurality of ribs, mutually hinging or interlocking parts, and a plurality of repeating units operatively connected to one another, and
wherein the eyewear comprises a first groove defined in and extending through the first rim, the first flexible element, and the first temple piece, wherein the first groove is defined in an inner surface of the first temple piece adjacent the first flexible element, and
wherein the eyewear comprises a second groove defined in and extending through the second rim, the second flexible element, and the second temple piece, wherein the second groove is defined in an inner surface of the second temple piece adjacent the second flexible element, wherein at least one of the first flexible element or the second flexible element is configured to form an open channel that is a part of at least one of the first groove or the second groove.

16. A method for manufacturing eyewear configured for receiving a hose, wherein the method comprises the steps of:

obtaining a digital file representing an eyewear design of the eyewear according to claim 15, and building the eyewear by an additive manufacturing (AM) process.

\* \* \* \* \*